(12) United States Patent
Pirzada

(10) Patent No.: US 8,015,972 B2
(45) Date of Patent: Sep. 13, 2011

(54) SYSTEM, DEVICE AND PROCESS FOR REMOTELY CONTROLLING A MEDICAL DEVICE

(76) Inventor: Shahzad Pirzada, Manhasset, NY (US)

( * ) Notice: Subject to any disclaimer, the term of this patent is extended or adjusted under 35 U.S.C. 154(b) by 1225 days.

(21) Appl. No.: 11/618,816

(22) Filed: Dec. 30, 2006

(65) Prior Publication Data

US 2007/0155208 A1  Jul. 5, 2007

Related U.S. Application Data

(60) Provisional application No. 60/756,184, filed on Jan. 3, 2006.

(51) Int. Cl.
*F16K 31/02* (2006.01)

(52) U.S. Cl. ............. 128/204.21; 128/204.18; 700/282

(58) Field of Classification Search .............. 128/204.18–204.29, 205.11, 205.12; 600/529; 700/282
See application file for complete search history.

(56) References Cited

U.S. PATENT DOCUMENTS

| | | |
|---|---|---|
| 201,728 A | 3/1878 | White |
| 2,597,751 A | 5/1952 | Ruge |
| 2,936,083 A | 5/1960 | Dahlman |
| 3,081,519 A | 3/1963 | Blades et al. |
| 3,151,306 A | 9/1964 | Hines |
| 3,217,818 A | 11/1965 | Engelsher et al. |
| 3,338,323 A | 8/1967 | Swersey |
| 3,439,524 A | 4/1969 | Rogers |
| 3,653,083 A | 4/1972 | Lapidus |
| 3,665,169 A | 5/1972 | Henderson et al. |
| 3,722,611 A | 3/1973 | Trikkonen |
| 3,742,329 A | 6/1973 | Giguere |
| 3,770,069 A | 11/1973 | Loshbough |
| 3,777,828 A | 12/1973 | Dietemeyer |
| 3,778,851 A | 12/1973 | Howorth |

(Continued)

OTHER PUBLICATIONS

International Search Report for Pirzada 3, Jun. 26, 2008.
International Search Report for Pirzada 9, Apr. 28, 2008.
Office Action in Pirzada 3 (U.S. Appl. No. 10/939,816), non-final rejection, Jul. 18, 2006/ copending related application.

(Continued)

*Primary Examiner* — Justine Yu
*Assistant Examiner* — Si Lee
(74) *Attorney, Agent, or Firm* — Collard & Roe, P.C.

(57) ABSTRACT

A system for controlling medical devices, wherein this system can comprise a device having at least one wireless or cellular based communication module. The module can be in the form of a GPRS module associated with a SIM card, or a CDMA module. The SIM card can be adapted such that it contains additional memory for storing a program for controlling the device or the system. Multiple cellular communication modules can also be installed in this system. Additional communication modules such as wireless modules including but not limited to Bluetooth, IRDA, RF, or any other wireless module can also be incorporated into the system. Wired modules can also be used, for example these wired modules can be RS-232 modules, USB, Serial adapters, phone and fax modem. Other modules can include audio modules such as speaker and microphone jacks, and video modules such as a camera for processing video readings. All of these components can be installed on a first side of a motherboard, which is disposed inside of a housing. The other side of the motherboard can have particular functional elements installed thereon. These functional elements can include a flow meter, and/or a electromechanical valve. All of these components can be controlled by one or more processor coupled to the motherboard. When this device is coupled to an ordinary PAP machine, such as a CPAP machine, it can be used to turn an ordinary PAP machine into an auto-adjust PAP machine or a BiPAP machine.

18 Claims, 20 Drawing Sheets

U.S. PATENT DOCUMENTS

| | | | |
|---|---|---|---|
| 3,822,425 A | 7/1974 | Scales | |
| 3,875,599 A | 4/1975 | Mracek et al. | |
| 3,986,012 A | 10/1976 | Loshbough et al. | |
| 4,036,318 A | 7/1977 | Nyholm | |
| 4,371,997 A | 2/1983 | Mattson | |
| 4,435,864 A | 3/1984 | Callaway | |
| 4,477,935 A | 10/1984 | Griffin | |
| 4,600,067 A | 7/1986 | Artigue et al. | |
| 4,644,597 A | 2/1987 | Walker | |
| 4,662,012 A | 5/1987 | Torbet | |
| 4,686,722 A | 8/1987 | Swart | |
| 4,768,250 A | 9/1988 | Kato | |
| 4,797,962 A | 1/1989 | Goode | |
| 4,838,257 A * | 6/1989 | Hatch | 128/204.18 |
| 4,848,492 A | 7/1989 | Hubbard et al. | |
| 4,864,671 A | 9/1989 | Evans | |
| 4,883,051 A * | 11/1989 | Westenskow et al. | 128/204.21 |
| 4,888,836 A | 12/1989 | Calderwood | |
| 4,907,307 A | 3/1990 | Weitzler | |
| 4,908,895 A | 3/1990 | Walker | |
| 4,914,760 A | 4/1990 | Hargest et al. | |
| 4,942,635 A | 7/1990 | Hargest et al. | |
| 4,967,431 A | 11/1990 | Hargest et al. | |
| 4,969,112 A | 11/1990 | Castle | |
| 4,982,466 A | 1/1991 | Higgins et al. | |
| 4,989,283 A | 2/1991 | Krouskop | |
| 4,992,775 A | 2/1991 | Castle et al. | |
| 5,020,176 A | 6/1991 | Dotson | |
| 5,029,352 A | 7/1991 | Hargest et al. | |
| 5,033,133 A | 7/1991 | Nissen | |
| 5,036,559 A | 8/1991 | Hargest | |
| 5,052,067 A | 10/1991 | Thomas et al. | |
| 5,070,560 A | 12/1991 | Wilkinson | |
| 5,079,785 A | 1/1992 | Garcia | |
| 5,086,856 A | 2/1992 | Heggstrom | |
| 5,090,076 A | 2/1992 | Guldager | |
| 5,090,077 A | 2/1992 | Caden et al. | |
| 5,092,415 A | 3/1992 | Asano | |
| 5,103,519 A | 4/1992 | Hasty | |
| 5,129,115 A | 7/1992 | Higgins et al. | |
| 5,142,717 A | 9/1992 | Everard et al. | |
| 5,228,485 A | 7/1993 | Lewis et al. | |
| 5,249,318 A | 10/1993 | Loadsman | |
| 5,267,364 A | 12/1993 | Volk | |
| 5,279,010 A | 1/1994 | Ferrand et al. | |
| 5,375,273 A | 12/1994 | Bodine, Jr. | |
| 5,388,292 A | 2/1995 | Stinson et al. | |
| 5,421,044 A | 6/1995 | Steensen | |
| 5,458,137 A | 10/1995 | Axe et al. | |
| 5,487,196 A | 1/1996 | Wilkinson | |
| 5,487,197 A | 1/1996 | Iskra et al. | |
| 5,499,417 A | 3/1996 | Wang | |
| 5,535,738 A | 7/1996 | Estes et al. | |
| 5,539,942 A | 7/1996 | Melou | |
| 5,540,219 A | 7/1996 | Mechlenburg et al. | |
| 5,542,136 A | 8/1996 | Tappel | |
| 5,560,057 A | 10/1996 | Madsen et al. | |
| 5,584,085 A | 12/1996 | Banko | |
| 5,586,346 A | 12/1996 | Stacy et al. | |
| 5,594,963 A | 1/1997 | Berkowitz | |
| 5,611,096 A | 3/1997 | Bartlett et al. | |
| 5,630,237 A | 5/1997 | Ku | |
| 5,634,224 A | 6/1997 | Gates | |
| 5,634,225 A | 6/1997 | Miller, Sr. et al. | |
| 5,659,908 A | 8/1997 | Nishino | |
| 5,685,036 A | 11/1997 | Kopfstein et al. | |
| 5,687,717 A | 11/1997 | Halpern et al. | |
| 5,699,570 A | 12/1997 | Wilkinson et al. | |
| 5,708,999 A | 1/1998 | Priolo et al. | |
| 5,717,603 A | 2/1998 | McClendon et al. | |
| 5,787,531 A | 8/1998 | Pepe | |
| 5,794,288 A | 8/1998 | Soltani et al. | |
| 5,802,640 A | 9/1998 | Ferrand et al. | |
| 5,850,644 A | 12/1998 | Hsia | |
| 5,853,005 A | 12/1998 | Scanlon | |
| 5,861,582 A | 1/1999 | Flanagan et al. | |
| 5,873,137 A | 2/1999 | Yavets-Chen | |
| D408,308 S | 4/1999 | De Brecourt | |
| 5,893,184 A | 4/1999 | Murphy | |
| 5,894,926 A | 4/1999 | Stafford et al. | |
| 5,898,963 A | 5/1999 | Larson | |
| 5,906,205 A | 5/1999 | Hiebert | |
| 5,920,934 A | 7/1999 | Hannagan et al. | |
| 5,931,791 A | 8/1999 | Saltzstein et al. | |
| 5,962,792 A | 10/1999 | Kimerer et al. | |
| 5,970,545 A | 10/1999 | Garman et al. | |
| 5,983,429 A | 11/1999 | Stacy et al. | |
| 5,987,325 A * | 11/1999 | Tayloe | 455/435.2 |
| 5,990,423 A | 11/1999 | Ashpes et al. | |
| 6,014,784 A | 1/2000 | Taylor et al. | |
| 6,047,423 A | 4/2000 | Larson | |
| 6,065,166 A | 5/2000 | Sharrock et al. | |
| 6,092,249 A | 7/2000 | Kamen et al. | |
| 6,093,895 A | 7/2000 | Niosi | |
| 6,108,843 A | 8/2000 | Suzuki et al. | |
| 6,122,785 A | 9/2000 | Bondie et al. | |
| 6,148,461 A | 11/2000 | Cook et al. | |
| 6,155,347 A | 12/2000 | Mills | |
| 6,180,893 B1 | 1/2001 | Salgo | |
| 6,269,811 B1 | 8/2001 | Duff et al. | |
| 6,287,252 B1 | 9/2001 | Lugo | |
| 6,347,553 B1 | 2/2002 | Morris et al. | |
| 6,349,724 B1 | 2/2002 | Burton et al. | |
| 6,405,496 B1 | 6/2002 | Stewart et al. | |
| 6,412,129 B1 | 7/2002 | Wu | |
| 6,454,724 B1 | 9/2002 | Greene | |
| 6,467,477 B1 | 10/2002 | Frank et al. | |
| 6,564,411 B2 | 5/2003 | Pirzada | |
| 6,649,849 B2 | 11/2003 | Bass et al. | |
| 6,715,171 B2 | 4/2004 | Grabe | |
| 6,721,980 B1 | 4/2004 | Price et al. | |
| 6,725,165 B1 | 4/2004 | Knox et al. | |
| 6,789,283 B2 | 9/2004 | Pirzada | |
| 6,804,558 B2 * | 10/2004 | Haller et al. | 607/30 |
| D499,425 S | 12/2004 | Pirzada | |
| 6,875,932 B2 | 4/2005 | Tuft | |
| 6,910,481 B2 | 6/2005 | Kimmel et al. | |
| 7,225,809 B1 * | 6/2007 | Bowen et al. | 128/204.21 |
| 7,261,691 B1 | 8/2007 | Asomani | |
| 7,316,648 B2 | 1/2008 | Kelly et al. | |
| 2001/0052152 A1 | 12/2001 | Soltani et al. | |
| 2002/0148046 A1 | 10/2002 | Pirzada | |
| 2003/0159219 A1 | 8/2003 | Harrison et al. | |
| 2003/0200611 A1 | 10/2003 | Chaffee | |
| 2003/0208849 A1 | 11/2003 | Wilkinson | |
| 2004/0102683 A1 | 5/2004 | Khanuja et al. | |
| 2004/0143677 A1 | 7/2004 | Novak | |
| 2004/0144383 A1 * | 7/2004 | Thomas et al. | 128/204.18 |
| 2004/0187871 A1 * | 9/2004 | Kimmel et al. | 128/204.23 |
| 2004/0200206 A1 | 10/2004 | Hall | |
| 2005/0060202 A1 | 3/2005 | Taylor et al. | |
| 2005/0112325 A1 | 5/2005 | Hickle | |
| 2005/0133027 A1 | 6/2005 | Elaz et al. | |
| 2005/0137653 A1 | 6/2005 | Friedman et al. | |
| 2005/0188991 A1 | 9/2005 | Sun et al. | |
| 2005/0228245 A1 | 10/2005 | Quy | |
| 2005/0247315 A1 | 11/2005 | Estes et al. | |
| 2005/0288571 A1 | 12/2005 | Perkins et al. | |
| 2006/0042627 A1 | 3/2006 | MacMillan et al. | |
| 2006/0124128 A1 | 6/2006 | Deane et al. | |
| 2006/0142648 A1 | 6/2006 | Banet et al. | |
| 2006/0150973 A1 | 7/2006 | Chalvignac | |
| 2006/0237002 A1 | 10/2006 | Bonney et al. | |
| 2006/0249160 A1 | 11/2006 | Scarberry et al. | |
| 2006/0264832 A1 | 11/2006 | Skwarek et al. | |

OTHER PUBLICATIONS

Office Action Mar. 8, 2007—Final rejection—Pirzada 3 (U.S. Appl. No. 10/939,816)/ copending related application.

Office Action Nov. 9, 2007— Non final rejection— Pirzada 3 RCE (U.S. Appl. No. 10/939,816)/ copending related application.

Office Action Mar. 25, 2008—Pirzada 6 (U.S. Appl. No. 11/164,655)/ copending related application.

* cited by examiner

Model Selection of CPAP

FIG. 10    Status Page of Medical Devices

Remote Control Page

Assigning Patient To Device Setup Page

SYSTEM, DEVICE AND PROCESS FOR REMOTELY CONTROLLING A MEDICAL DEVICE

REFERENCE TO RELATED APPLICATIONS

This application is a non provisional application and applicant claims priority from Provisional Application Ser. No. 60/756,184 filed on Jan. 3, 2006 wherein the disclosure of which is hereby incorporated herein by reference in its entirety.

BACKGROUND OF THE INVENTION

One embodiment of the invention relates to a remote controllable wireless system which can be used to control at least one medical device. This type system can include at least one SIM card and be controllable over a relatively long distance. Other types of devices for wirelessly communicating with equipment are known. For example, U.S. Patent Application Publication No. 2005/0228245 to Quy discloses a method and apparatus for health and disease management combining patient data monitoring with wireless internet connectivity. U.S. Patent Application Publication No. 2004/0143677 to Novak discloses a system for controlling medical devices using a high bandwidth data transmission protocol such as Ethernet or Bluetooth wherein the disclosures of both of these applications are hereby incorporated herein by reference.

Other devices can be used to interact with PAP machines such as CPAP machines, or BiPAP machines. For example, U.S. Patent Application Publication No. 2005/0188991 to Sun et al. discloses a positive airway pressure therapy management module. U.S. Pat. No. 6,349,724 to Burton et al. discloses a gas compression and delivery device, such as a BIPAP, CPAP or auto PAP device, wherein the disclosures of the SUN application and the Burton Patent are hereby incorporated herein by reference in their entirety.

Essentially PAP machines can be used to treat sleep apnea. Sleep apnea is a condition wherein a patient's airway becomes restricted as the patient's muscles relax naturally during sleep, which can wake a person from their sleep. The PAP machine can remedy this situation wherein the PAP machine delivers compressed or pressurized air to a face mask via a hose, so that unobstructed breathing becomes possible, reducing or preventing apneas or hypopneas. This pressurized air can be measured on the order of centimeters of water, (cm/$H_2O$) wherein a typical PAP machine can deliver pressures of 4 to 20 cm, or even up to 30 cm.

There are many different types of PAP machines such as Continuous Positive Airway Pressure machines (CPAP); Bi level positive airway pressure machines (BiPAP); Auto adjusting positive airway pressure machines (AutoPAP), or spontaneous time PAP machines. CPAP machines provide one constant pressure to the patient. BiPAP machines provide two levels of pressure wherein there is a first level for inhalation (IPAP) and a second level for exhalation (EPAP). An auto adjusting PAP machine automatically tunes the amount of pressure delivered to the patient to the minimum required amount to maintain an unobstructed airway, on a breath by breath basis. This device can be operated such that it measures the resistance of the patient's breathing, thereby giving the patient precise pressure required at a given moment and avoiding the compromise of fixed pressure.

The three basic components of a PAP device are a blower which is usually in the body of the device, a hose and a mask or interface which is connected to the body or blower via the hose.

SUMMARY

One embodiment of the invention is a system for controlling medical devices, wherein a device of this system comprises at least one wireless or cellular based communication module. The module can be in the form of a GPRS module, or a CDMA module. There is at least one Smart Identification card or SIM card associated with at least one of the GPRS modules. The SIM card can have additional memory for storing a program for controlling the device and/or the system itself. The SIM card can have even more memory for storing data concerning events of this system. This cellular communication can be beneficial because it allows the device to communicate with remote users without communicating through a computer network. In addition, this direct communication can be over cellular protocols which allow for a long distance control of a medical device.

The SIM card can be selectively removed from this device as well. This feature makes the device adaptable to allow different SIM cards to be installed and also allows for selective downloading or uploading information from the memory on the SIM card.

Multiple additional modules can also be installed in this system. For example, the system or device can further comprise additional communication modules such as wireless modules, including but not limited to Bluetooth, IRDA, RF, or any other wireless module. Wired modules can also be used, for example these wired modules can be RS-232 modules, USB, Serial adapters, phone and fax modem. Other modules can include audio modules such as speaker and microphone jacks, and video modules such as a camera for processing video readings. There can also be a GPS module which allows the location of this device to be tracked. In one embodiment, all of these components can be installed on a first side of a motherboard, which is disposed inside of a housing. The other side of the motherboard can have particular functional elements installed thereon. These functional elements can include a flow meter, and/or a electromechanical valve. All of these components can be controlled by one or more processor coupled to the motherboard. When this device is coupled to an ordinary PAP machine, such as a CPAP machine, it can be used to turn an ordinary PAP machine into an auto-adjust PAP machine or a BiPAP machine because it controls the air flow output via the valve.

For example, in one implementation of one embodiment of the invention, the device can be coupled in series with the body or blower of a PAP machine such as a CPAP machine, such that this device is positioned in series between the blower and the interface or mask to turn that ordinary PAP machine into an adjustable machine. The output pressure or air flow at the mask is then controlled by this device which regulates either the PAP machine itself or just the air or fluid flow between the PAP machine and the interface. This regulation occurs via the flow meter and the electromechanical valve.

In one embodiment, there are at least two cellular communication modules disposed on the motherboard. At least one cellular communication module is for communicating with an offsite server via telecommunication protocols. The information sent from the device can be diagnostic medical information read from a patient. Information sent from the server can be in the form of instructions which would be used to control the functional elements incorporated into the device to control the actions of the device. The additional cellular communication protocol can be used to call for emergency help, if either the device or the remote server determines that a patient's vital medical characteristics are outside of a predetermined set of parameters. In addition, if a relatively large amount of information is being transferred between the device and the server, resulting in relatively slow response times, the second or additional cellular communication module can be used to add effective bandwidth to transfer a portion of this relatively large amount of information in a more efficient and timely manner.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, wherein similar reference characters denote similar elements throughout the several views.

DETAILED DESCRIPTION OF PREFERRED EMBODIMENT

Figure 1A:
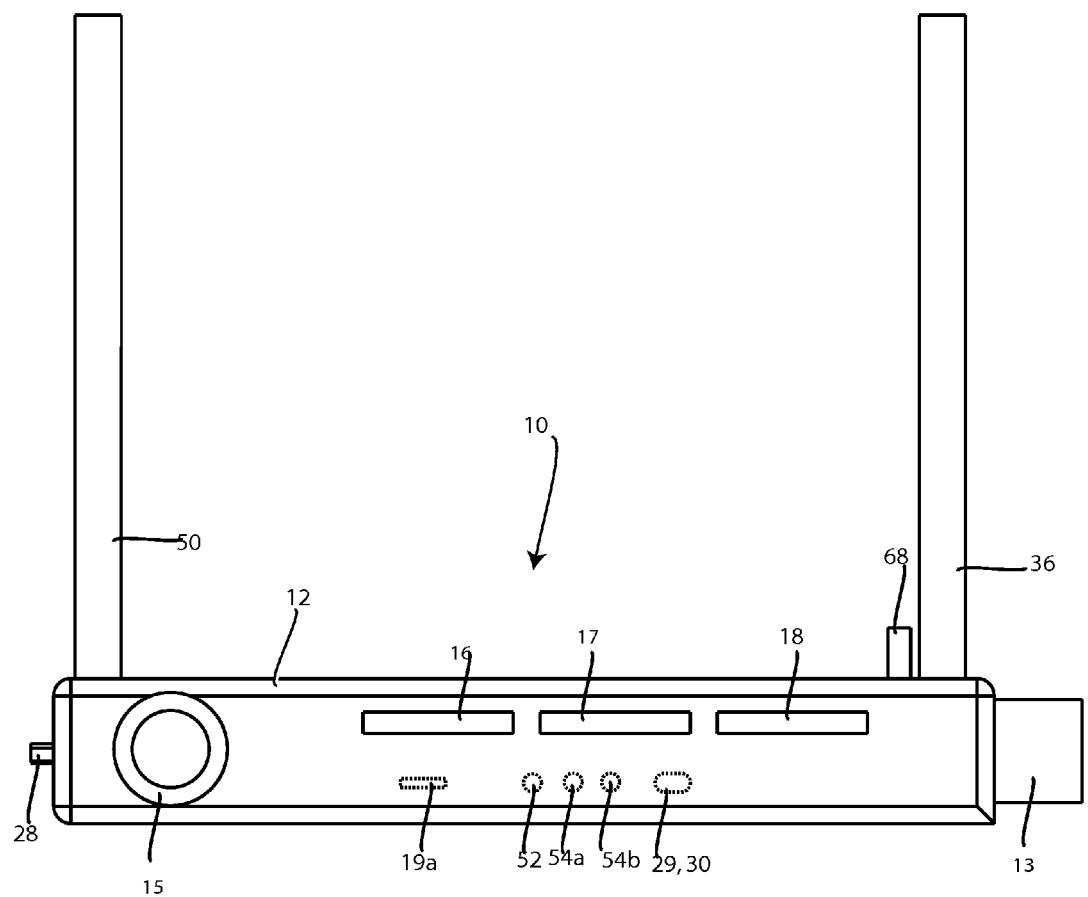
FIG. 1A is a front view of an embodiment which is representative of one embodiment of the invention.
Figure 1B:
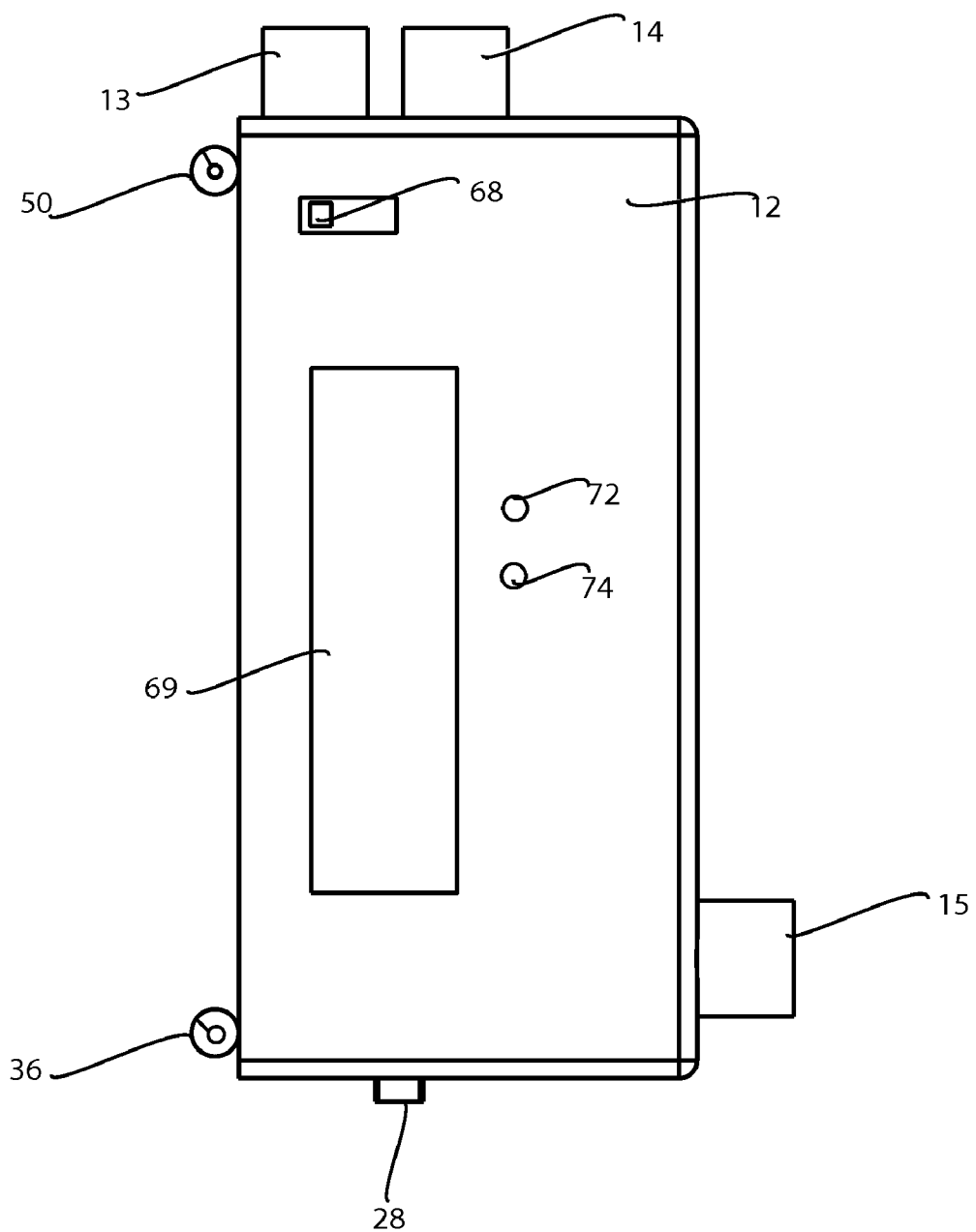
FIG. 1B is a top view of the device shown in FIG. 1A.
Figure 1C:
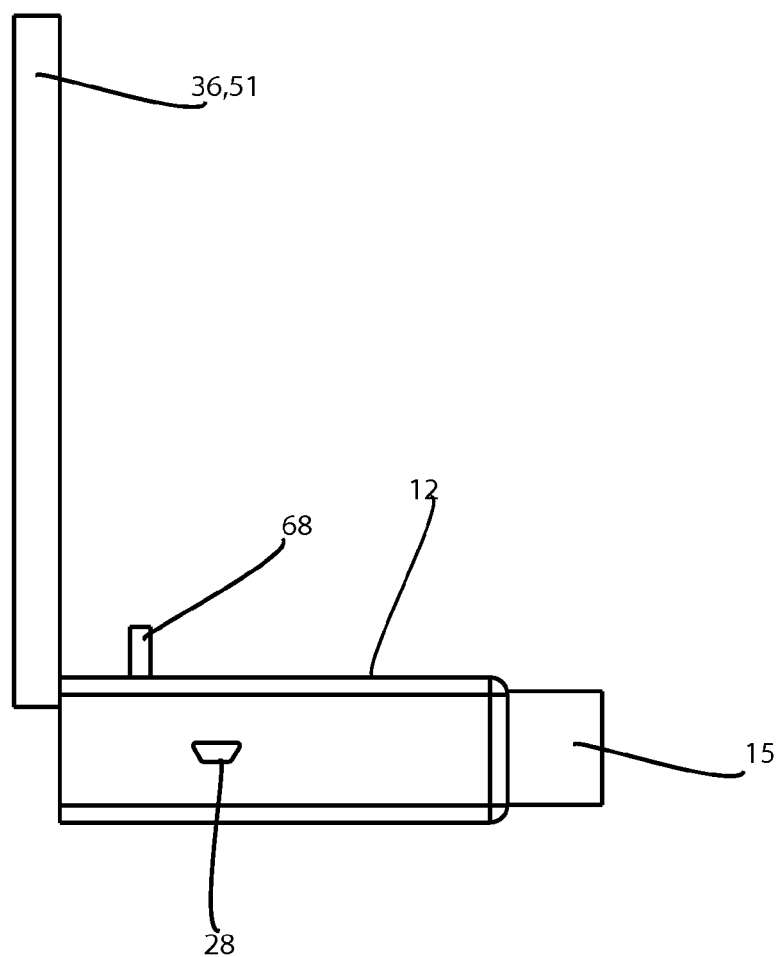
FIG. 1C is a left side view of the device shown in FIG. 1A.
Figure 1D:
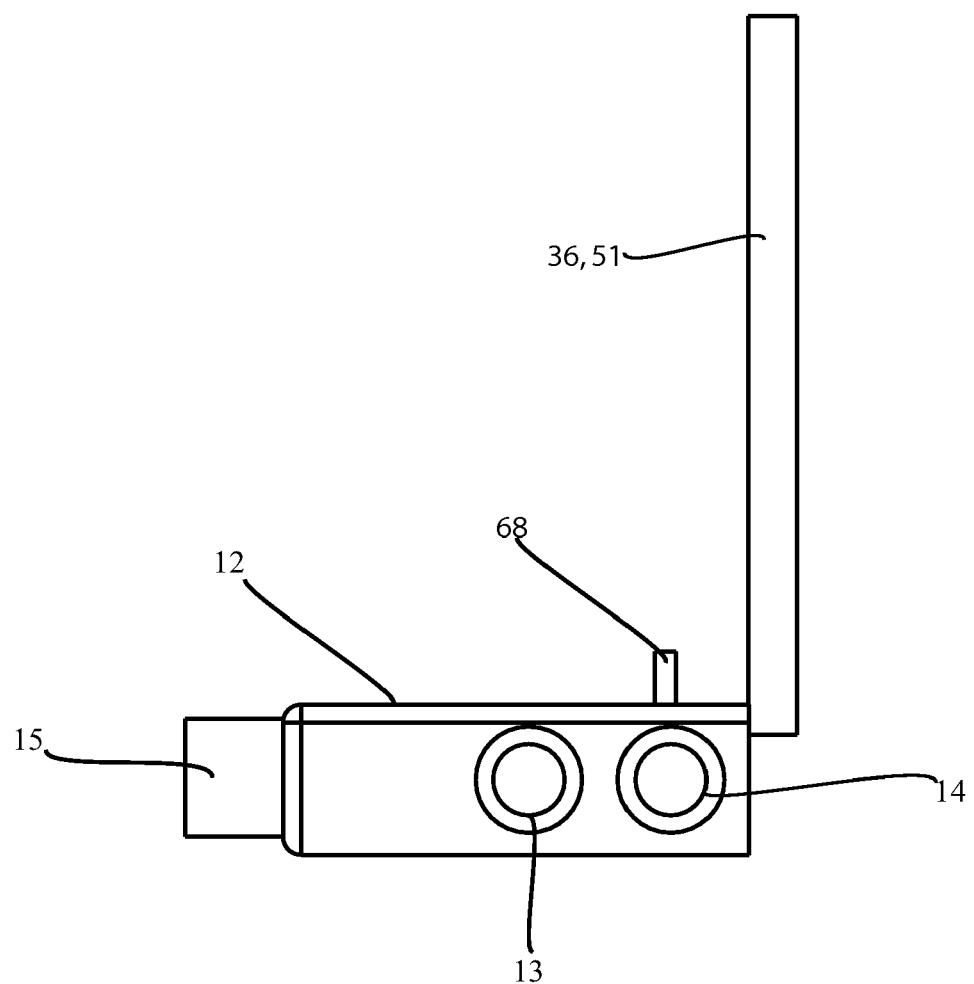
FIG. 1D is a right side view of the device shown in FIG. 1A.
Figure 2A:
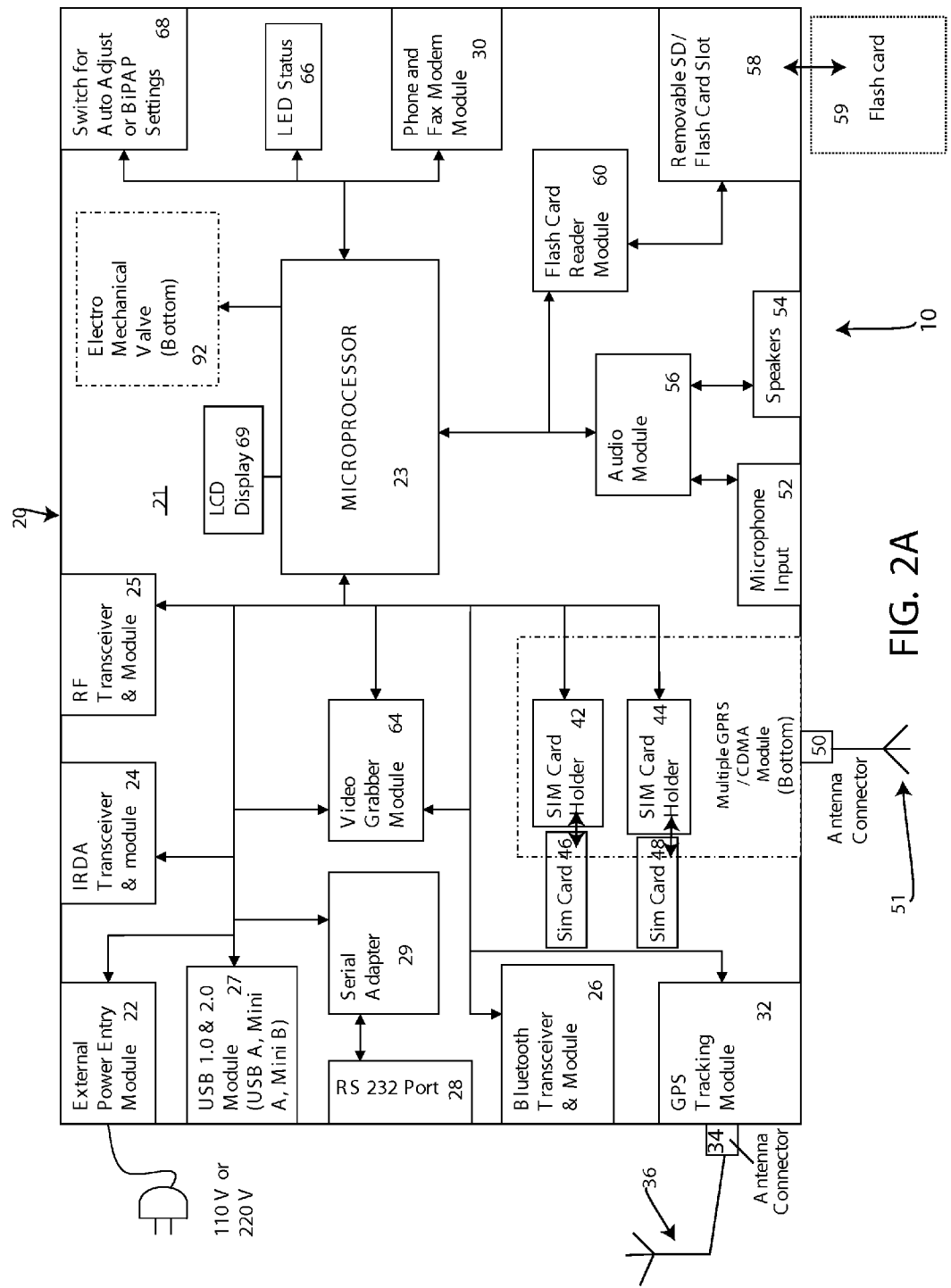
FIG. 2A shows a schematic block diagram view of a first side of a motherboard of the device.
Figure 2B:
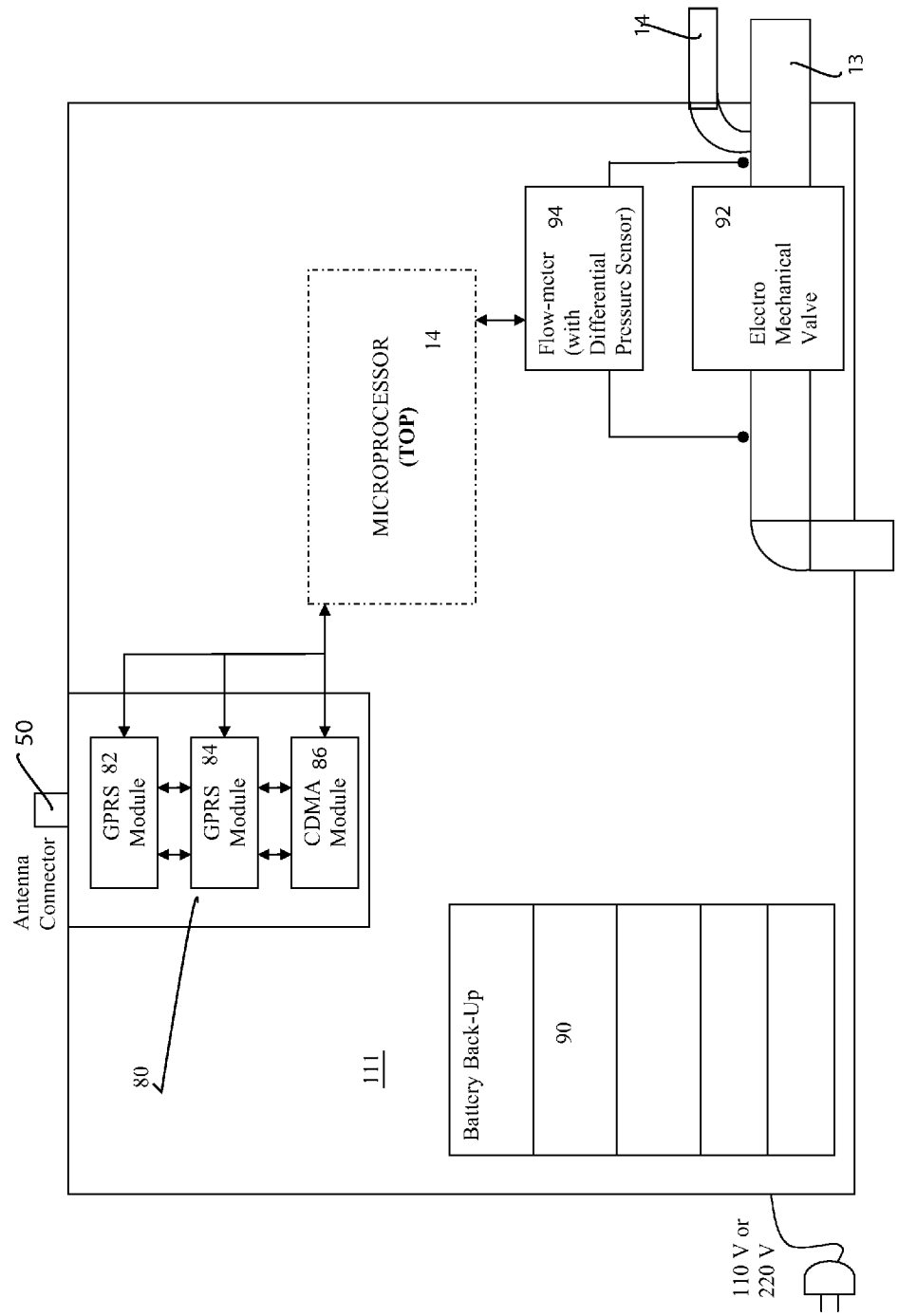
FIG. 2B shows a reverse side of the first side of the motherboard shown in FIG. 1.

FIG. 1A discloses a device 10 which is in the form of a compact unit for remote communication with a controlling station or computer, (See FIG. 5) wherein this device can be used to communicate with other electrical devices such as medical equipment. For example, this device includes a housing 12, at least two pump inputs 13, and 14, (See FIG. 1B) and a pump output 15. Pump input 13 can be used for connecting to a CPAP machine, while pump input 14 can be used to connect to any other type fluid input device such as an auxiliary pump. Pump output 15 can be coupled to a mask for allowing a user to breathe this air or fluid input. There can also be multiple slots such as three slots 16, 17, and 18 for allowing the input of different SIM cards and/or flash memory cards for enhancement of this device. Other input and output ports are also available such as a USB input 19a, or microphone input 52 (See FIG. 2A), speaker outputs 54a, and 54b, and any other type connection such as ports for serial adapter 29, or for a phone or fax modem 30, or an RS232 port 28 (See FIG. 3). Antennas 36 and 51 can also be coupled to and incorporated with device 10 for improved transmission and reception. These antennas are coupled to antenna connectors 34 and 50 (See FIG. 2A). FIGS. 1B, 1C, and 1D also disclose different sides of this device 10. For example, from these different sides, there is shown switch 68 (See FIG. 2A) and LED display 69 for displaying the status of device 10. FIG. 2A shows a schematic block diagram view of the communication device 10 comprising a double sided circuit board or motherboard 20. The first side 21 of circuit board 20 is shown in FIG. 2A while the second side is shown in FIG. 2B. Alternatively, in a less compact form, the two sides shown in FIGS. 2A and 2B can be formed on two separate motherboards which are in communication with each other.

Motherboard 20 is powered by an external power module 22. External power entry module 22 can be connected to a cord which can be for example a 110 V or 220 V to connection for providing power to motherboard 20. Alternatively, motherboard 20 can be powered by battery backup 90 (See FIG. 2B).

A microprocessor 23, is coupled to motherboard 20, wherein microprocessor 23 can control all the elements on this device. Microprocessor 23 is in communication either directly or indirectly with each of the components coupled to this motherboard. Microprocessor 23 can be any type of suitable microprocessor. In one embodiment, microprocessor 23 has a PPP B IP B TCP stack encryption which includes a link control protocol (LCP) Layer, and Internet protocol control protocol (IPCP). This processor also has a layer password authentication control protocol or LCP, a layer and Internet protocol IP and a transfer control protocol TCP. There is also an encryption layer or simple permanent key encryption, an application layer or FTP or similar, and a firmware which will give commands to the rest of the board.

In addition, there can be a series of optional communication elements coupled to this board. For example, there can be a plurality of transceivers including IRDA transceiver module 24 and a RF transceiver module 25, or a bluetooth transceiver module 26. The IRDA transceiver module 24 can be used to communicate with all IRDA ready commercial devices with an external IRDA module connected via any known IRDA connection method. The RF transceiver module 25 can be used to communicate with all RF-ready commercial devices or all commercial devices with an RF module connected via radio frequency. With regard to the Bluetooth module 26, this module 26 can communicate with all commercial Bluetooth dongle, all commercial devices with built-in Bluetooth and Bluetooth ready commercial devices that are connected to Bluetooth dongle externally. Other known wireless communication modules or elements could also be used. These devices are for communicating wirelessly with other devices such as medical devices for wireless communication.

Other optional communication modules can include wired communication modules. For example, there can also be any one of a USB module 27, a RS-232 port 28, a serial adapter 29, and a phone and fax modem module 30. Any other known communication modules could also be used as well. For example, the USB module could be used to support a USB a connection, or a USB b connection in communication between all commercial devices that are USB ready or have a USB port which enable users to communicate via the USB port. In addition, the RS-232 port 28 has a serial adapter which can be in communication between all RS-232 serial port ready commercial devices. The phone and fax modem module 30 can include an RJ 11 connector connected to the wall socket of the telephone line where this will enable automatic dialing to customized remote server transfer data via dial-up connection. With this type of communication, this data can then be fax data that is in the memory the board in a text format that is being generated by the micro-controller 14 to a remote fax machine.

Furthermore, to assist in locating this device, there can be a GPS tracking module 32. All of these wireless elements can communicate with the assistance of antenna connector 34 which connects to an antenna 36, or antenna connector 50 which connects to antenna 51.

Figure 2C:
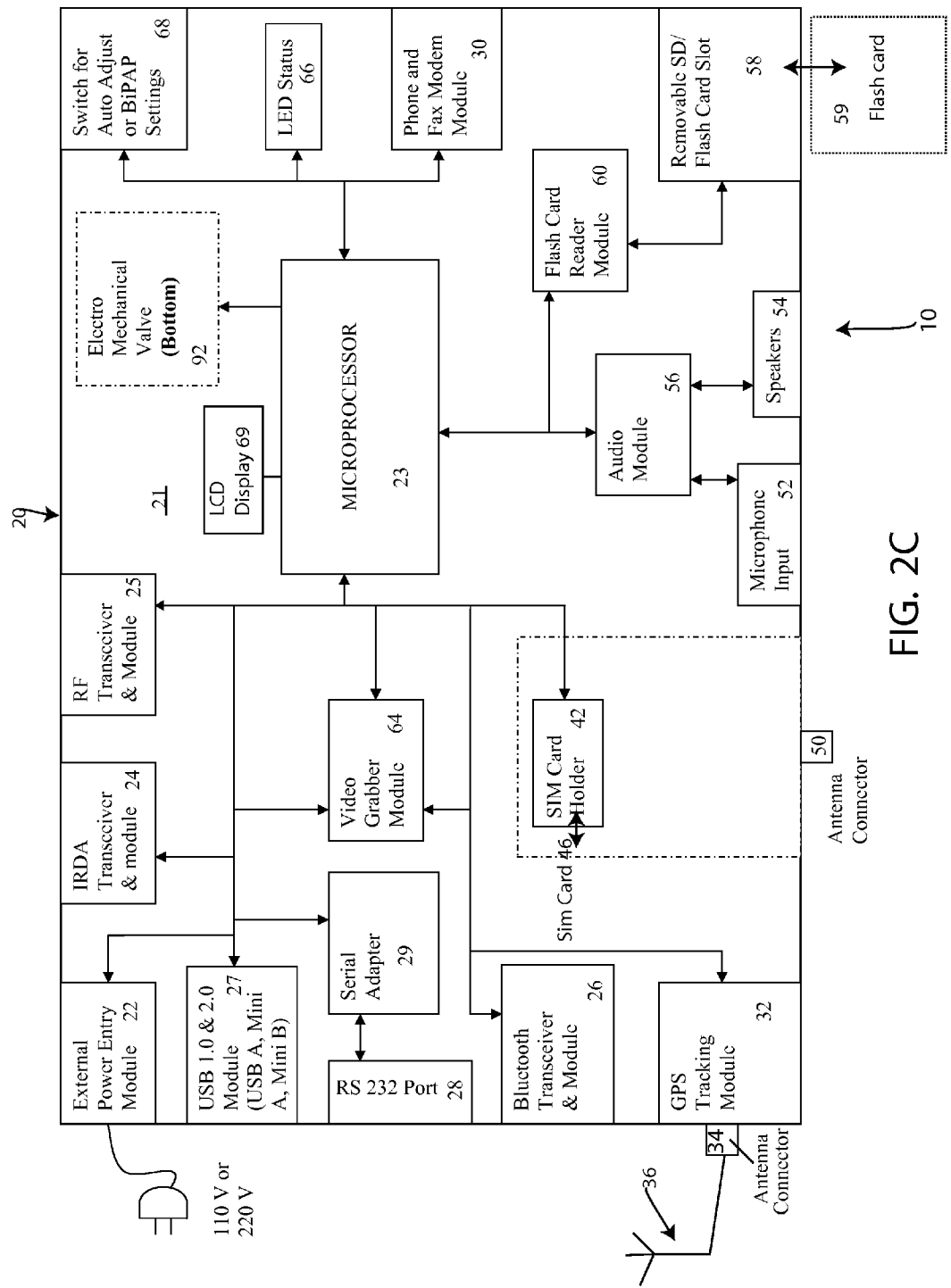
FIG. 2C shows another embodiment of the first side of the motherboard shown in FIG. 2A.

Coupled to motherboard 20 is a SIM card module 40 which includes SIM cardholders 42 and 44 for holding SIM cards 46 and 48. In this case, at least one SIM card 46 would be used. FIG. 2C shows a similar embodiment wherein only one SIM card 46 and only one SIM card holder 42 is used. Any additional SIM card such as SIM card 48 would be in optional addition to this system. Each SIM card can be used as a removable memory, to store a patient profile and patient data besides storing GSM information. In addition, each SIM card is adapted such that it can store a relatively large amount of data such as 1 Gigabyte (GB), 2 GB, and up. In this case, each SIM card can contain one or more phone numbers or allow one or more GPRS modules to connect to it, to increase bandwidth while transmitting packet files to a remote server (See FIG. 4). This information can include live video and audio which can be captured by video grabber module 64, and audio module 56. Each of these SIM cards is removable and insertable into another board for allowing for easy data retrieval, and allowing each of these SIM cards to be interchangeable with multiple devices.

An audio module 56, as disclosed above, is an optional module and is coupled to motherboard 20 and also to microprocessor 23. Audio module 56 is in communication with microphone input 52 and speakers 54. In addition, there can be an optional flash card reader module 60 which is in communication with microprocessor 23 and which is in communication with removable SD flash card slot 58. In this case, a flash card can be inserted into this flash card slot 58 wherein this flash card 59 can be read through flash card reader module 60. This information can then be sent to microprocessor 23.

There is also an optional switch for auto-adjust for connection to a BIPAP or CPAP machine 68, as well as an optional indicator LED 66 to indicate whether the switch is turned on. Both of these components are in communication with microprocessor 23. Switch 68 can be used so that when a user turns on switch 68, device 10 is now activated and monitors a user's breathing and controls the airflow into the user thereby turning a generic CPAP machine into a BiPAP or an automatically adjusting CPAP machine.

In addition, there can be an optional electro-mechanical valve 92 which is also in communication with microprocessor 23. Electro-mechanical valve 92 is shown in greater detail in FIG. 2B.

FIG. 2B discloses a reverse side of motherboard 20. In this view, there are three optional communication modules. For example, there is a GPRS module 82, a second GPRS module 84 and a CDMA module 86 which are all in connection with microprocessor 23.

This board is designed with multiple GPRS modules and/or multiple CDMA modules so that it creates a system having multiple channels or lines and improved bandwidth. In addition, this multiple GPRS module system allows for a redundancy in dialing and transmission failure backup. Furthermore, this multiple GPRS module allows for multiple user access wherein each user is dedicated to each GPRS module which is associated with a SIM card. For example, each SIM card is associated with an associated GPRS module which creates individual communication elements for communicating through these gateways.

This GPRS/CDMA module allows for different data streams to be split among the different protocols. For example, one communication module can transmit a blood pressure (BP) value, another communication module can transmit an oxygen value, while another module can be used for video and audio streaming over the web.

These modules are also in communication with an antenna connector 34 and/or 50 (See FIG. 2A) which can be connected to an antenna.

In addition, on this side of motherboard 20, is a battery backup 90, which is in communication with external power entry module 12 which is connected to cord 13.

With this design, either one of SIM cards 46 or 48 can be adapted such that they also hold additional flash memory for running a program for controlling microprocessor 23. For example, a first SIM card 46 can be designed to have additional memory to store a program for controlling the components on board 20. A second SIM card 48 can be used to store additional data received by this device relating to any one of the additional connected medical devices. Alternatively, a first SIM card 46 can also be used to store the data as well. This data is then relayed via a communication protocol such as GPRS or CDMA to a remote monitoring device.

Figure 5:
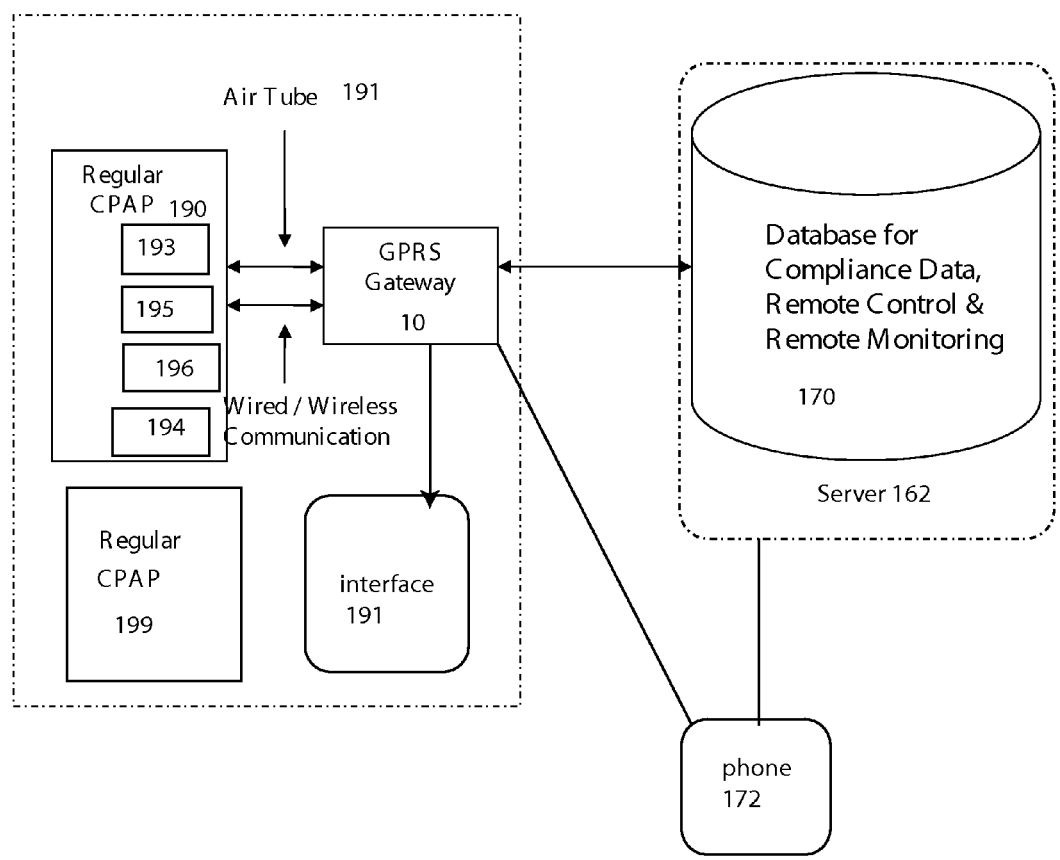
FIG. 5 discloses one implementation of the device for use with CPAP machines.

Furthermore, with this design, the double-sided motherboard is convenient in that it allows for the positioning of a communication and/or controlling device to be disposed in a first side 21 of the motherboard 20, while a controlling device, such as electro-mechanical valve 92 or a flowmeter 94 can be disposed on an opposite side. Electro mechanical valves 92 and flowmeters 94 can be useful components to a system which is used to control a standard CPAP machine such as shown in FIG. 5. Because the electromechanical valves 92 and the flowmeter 94 can require a relatively large amount of space relative to the other electronic components, the double sided motherboard 20 can serve as a useful space saving feature.

In addition, the first side 21 of motherboard 20 can be formed as a communication and overall control module, while the second side can be used as a particular medical device controller.

For example, for ease of manufacture, the first side 21 can be produced as a set unit, multiple times for controlling any type of medical device. However, the opposite side or the second side 111 of motherboard 20 can be customized for controlling particular medical devices or machines such as a CPAP machine.

Microprocessor 23 can also work with SIM cards 46 and 48 to detect and switch among the different SIM cards based upon signal strength to provide a more efficient means of communication. In this case, if microprocessor 23, detects a weak signal on any one of the GPRS or CDMA modules, microprocessor 23 can then switch to another communication module that includes a stronger signal.

In addition, microprocessor 23 can also be used to reprogram either one of SIM cards 46 or 48 with any upgrades or any other features. In this case, firmware can then be downloaded into the system, and stored, on any one of these SIM cards 46 or 48 or flash memory such as flash card 59 to upgrade any software running on the system.

Microprocessor 23 can also be programmed to automatically call for help such as call 911, if a patient being monitored has vital signs that fall outside of predetermined guidelines. For example, with a dual SIM card system, a first SIM card such as SIM card 46 can be used to communicate between a monitoring system such as a server and a database 170 (See FIG. 7). The second SIM card such as SIM card 48 is then a free line which can then be used to automatically call either a medical provider or an emergency line if the remote monitoring system including database 170 reads that a patient is outside of any predetermined guidelines such as in critical condition.

Figure 3:
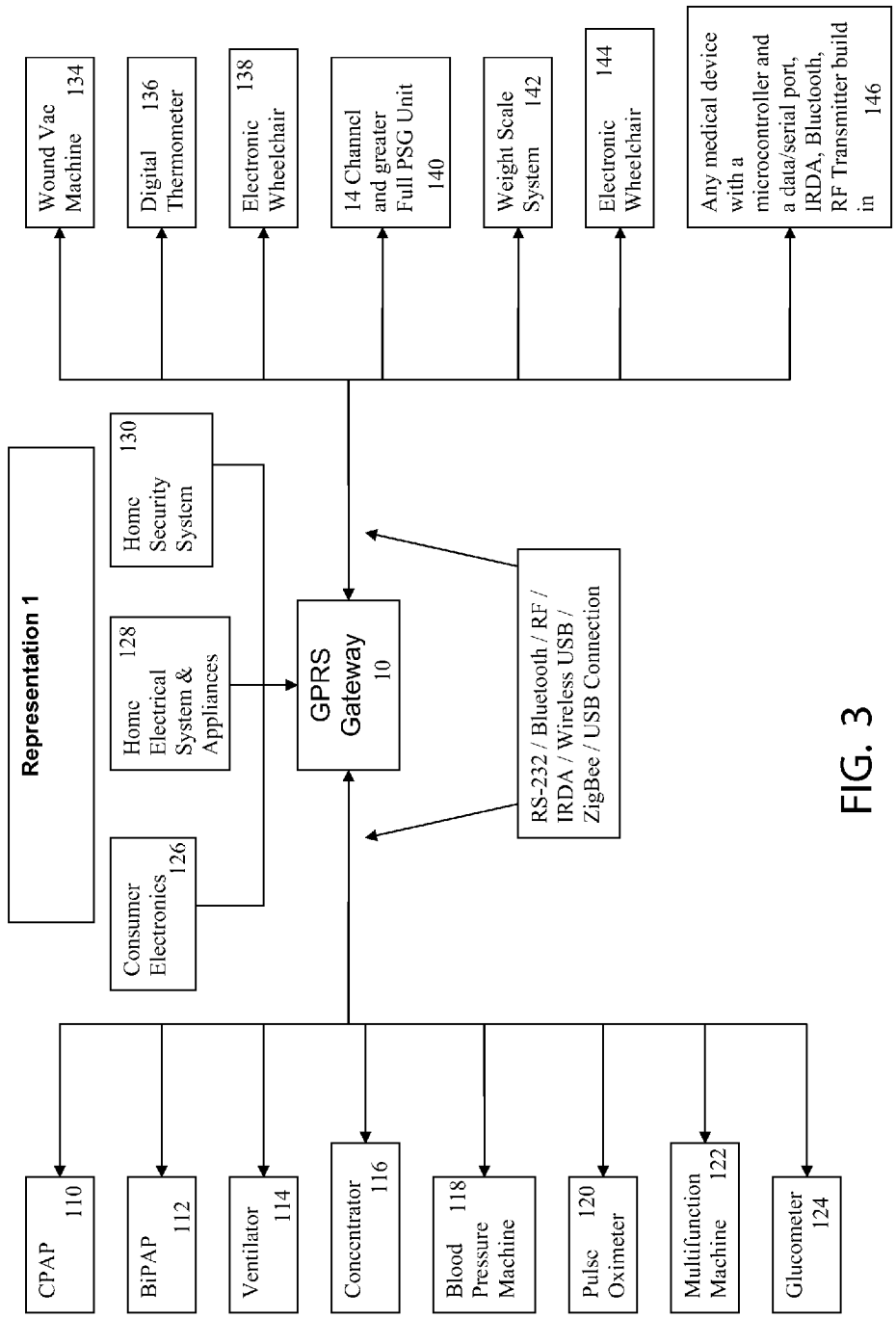
FIG. 3 discloses a schematic block diagram of the different means for the device of FIG. 1, connecting to different electronic or medical components.

FIG. 3 discloses a schematic block diagram of the different means for connecting to different electronic or medical components. For example, with this design, there can device 10 which forms a GPRS Gateway such as through device 10 which can be used to communicate with any number of devices. For example, device 10 can be used to communicate with either a CPAP machine 110, a BiPAP machine 112, a ventilator 114, a concentrator 116, a blood-pressure machine 118, a Pulse Oximeter120, a multifunction machine 122, or a Glucometer 124.

This device, such as device 10, can also communicate with different controlling devices such a consumer-electronics 126 home electrical system appliances 128 or home security systems 130.

This device can also selectively communicate with other different medical devices. For example device 10 can communicate with a Wound Vac machine 134, a digital thermometer 136, an electronic wheelchair 138, a 14 channel and greater full PSG unit 140, a weight scale system 142, an electronic wheelchair 144 or any other medical device that has a micro-controller and a data input and output that can meet that can indicate either wirelessly or in wired manner 146.

Because this portable medical communication device can communicate via a SIM card, this device can communicate with controlling elements such as personal computer from a far distance.

Figure 4:
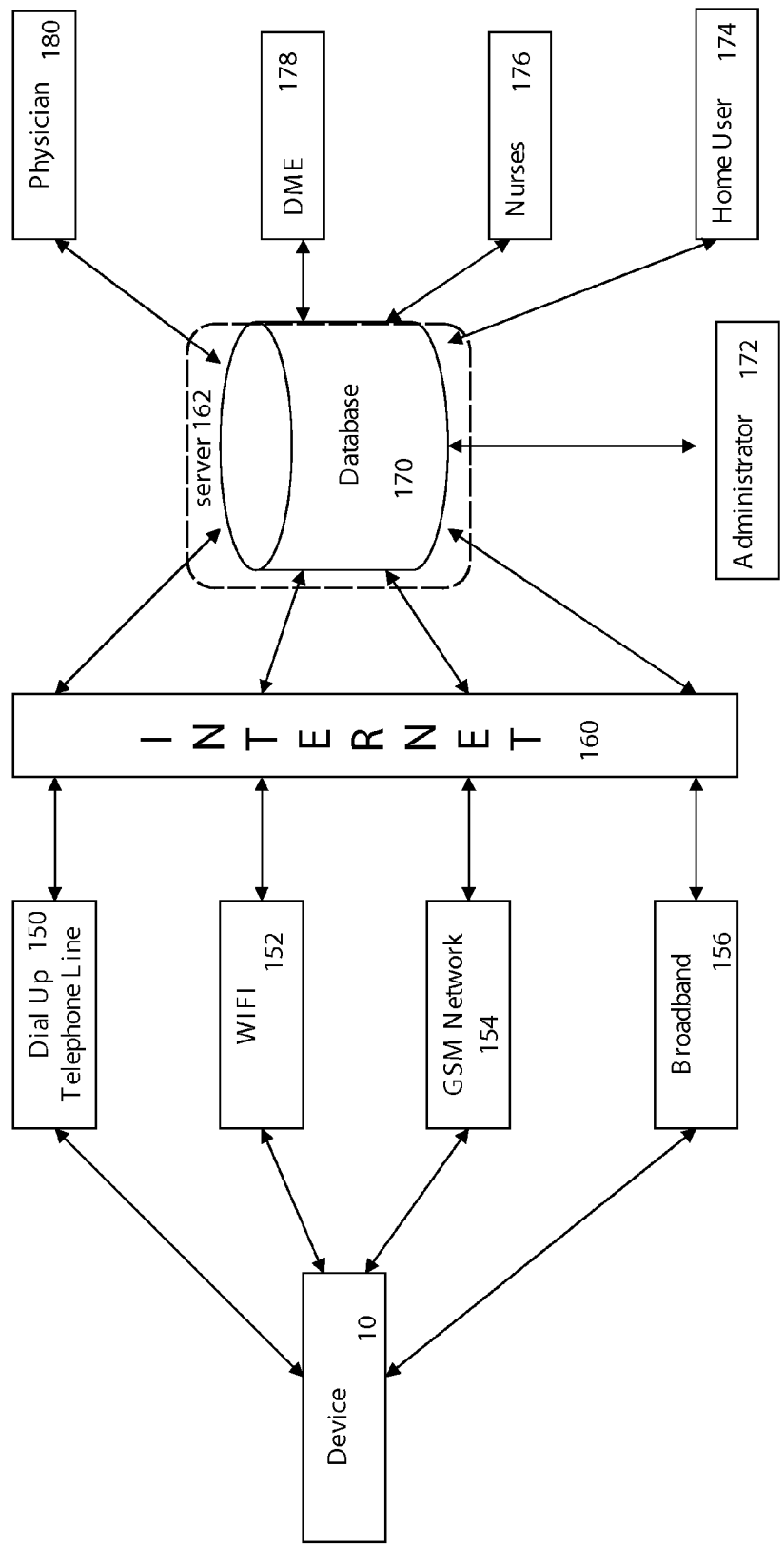
FIG. 4 discloses a schematic block diagram of the device of FIG. 1 which can communicate over a plurality of different communication protocols.

FIG. 4 discloses a schematic block diagram of the device 10 which can communicate over a plurality of different communication protocols. For example, device 10 can communicate over a dial-up telephone line 150, via WiFi communication 152, through GSM network or any cellular based telephone communication 154, or through broadband communication network 156. The SIM card can interact with the Internet 160 to communicate with an off-site database 170. Database 170 can be stored on a server 162 or any other type personal computer. In addition, a plurality of different users can also communicate through these communication protocols with database 170. For example a medical administrator 172 can be in communication with database 170, a home user can be in communication with database 170, nurses 176, DME (Durable medical equipment) 178, or physicians 180 can all be in communication with database 170 to review any diagnostics that are read from device 10 and then sent through Internet 160.

FIG. 5 discloses one implementation of the device 10. For example device 10 can be used to turn a regular CPAP 190 into an auto-adjust CPAP machine. This transformation can be through a Gateway device 10, wherein this device is in communication with database 170 for compliance data remote-control remote monitoring as disclosed in FIG. 4. As shown in FIG. 4, this communication can be through the Internet 160. As shown in this view, the connection between device 10 and a regular CPAP machine is formed such that it is in series with CPAP machine and a face mask. For example, with this design, device 10 is positioned between a regular CPAP machine 190 and a face mask or interface 191 on a patient. With this type of connection, all air or fluid flow from the CPAP machine 190 to a patient can be selectively controlled via device 10. In this case, when a user flips switch 68 to an on position, this turns device 10 on so that it now turns a normal CPAP or BiPAP machine into an automatically adjusting machine. In addition, device 10 can also be used to turn an ordinary CPAP machine into a BiPAP machine as well.

For example, to create an automatically adjusting CPAP or BIPAP machine, or to turn a CPAP machine into a BiPAP machine, the air flow or fluid flow setting can be turned to a relatively high level or to its highest level. The fluid or air flow from this machine 190 would then flow through a tube 192 such as a rubber hose and into input connection 13. This fluid or air would then flow through device 10 and be monitored by device 10 via flow-meter 94. The information that is read from flow-meter 94 would then be processed in microprocessor 23 and then sent to a server or remote computer 162 housing database 170. The information in this case can be sent via wireless telecommunication lines such as through a GPRS, or CDMA protocol, and through an associated GPRS module or CDMA module. Server or computer 162 in combination with database 170 would then read this information and determine whether to adjust the air flow through device 10. To adjust this air flow, server 162, would communicate wirelessly with either one of the GPRS modules 82, 84, or CDMA module 86 to send adjustment information to adjust electro-mechanical valve 92. Electro-mechanical valve 92 can operate such that it acts as a bleeder valve, which can selectively regulate the output pressure coming from output tube 15. Alternatively, device 10 can perform the analysis internally and then adjust the settings accordingly. Processor 23 then compares the readings of a patient with the parameters stored in the memory of device 10 to make the appropriate adjustments.

The constant regulation of this output pressure from output tube 15 thus turns a normal or regular CPAP 190 into an auto-adjust CPAP.

Communication between device 10 and CPAP machine 190 can be via any known communication protocol, such as through an RS232 protocol port, through a wireless communication such as through Bluetooth module 26, through serial adapter 29, USB port 27, IRDA transceiver module 24, or through RF transceiver module 25. In addition, while these protocols are options, other protocols could also be used. This communication could be to automatically adjust the blower output settings of a CPAP machine 199 to control the final output without being connected to device 10 via hoses. Any one of these CPAP machines can also include an associated processor 193, a wired connection module 194, a blower unit 195, or a wireless connection module 196.

Figure 6A:
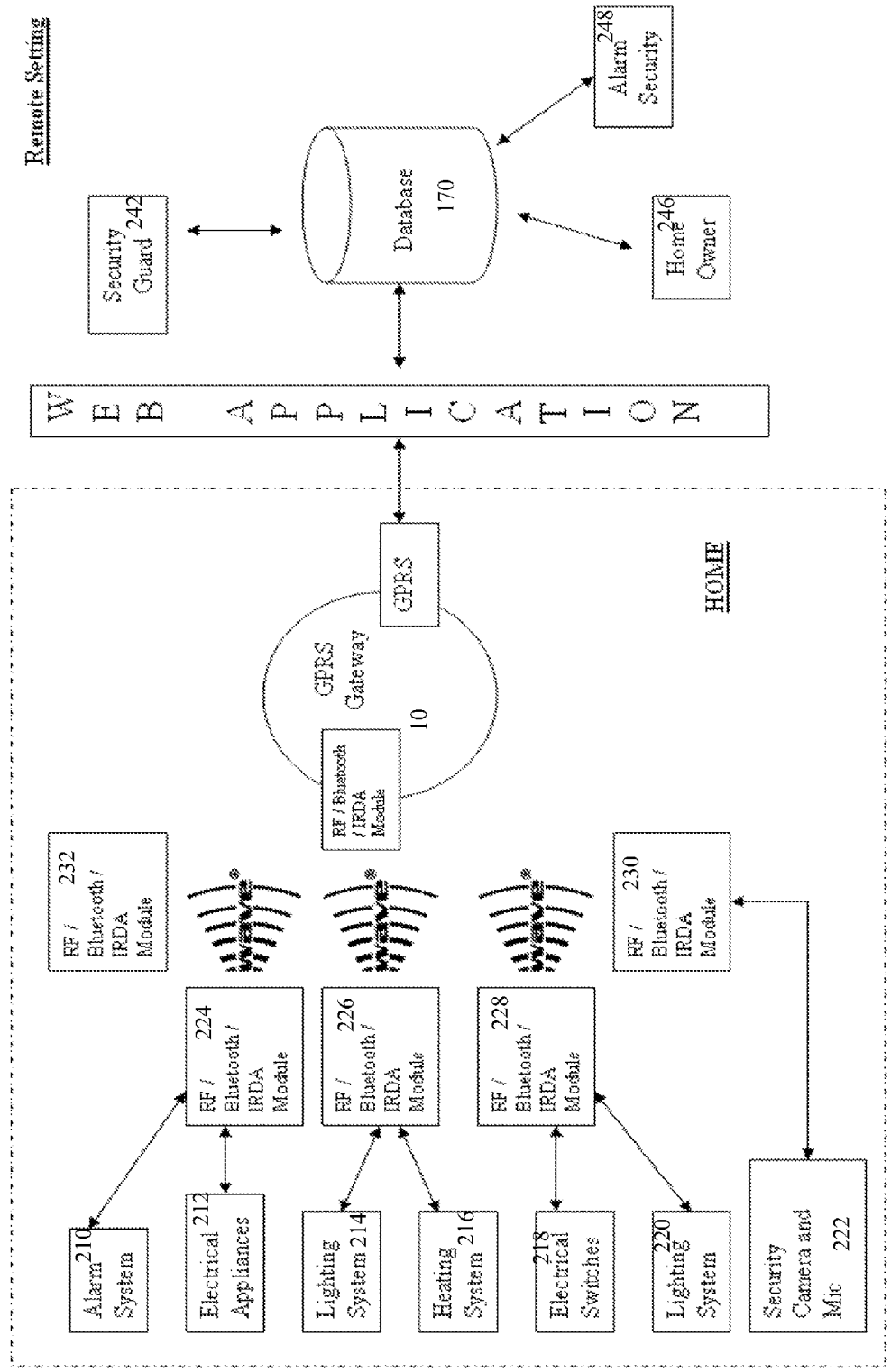
FIG. 6A discloses a schematic block diagram of a layout of a GPRS system which is in communication with web applications and a database.

FIG. 6A discloses a schematic block diagram of a layout of a GPRS system which is in communication with web applications 240 and database 170. These devices also include multiple wireless modules 224, 226, 228, 230, and 232.

Each of these wireless modules can be in communication with any other type of home medical device. For example, any one of these modules can be in communication with an alarm system 210, electrical appliances 212, lighting systems 214, heating systems 216, electrical switches 218, an additional lighting system 220, or a security camera and microphone 222.

In addition, database 170 can also be in communication with a security guard 242 homeowner 246 or an alarm security system 248. In this way, the GPRS system 10 can remotely control a house via web applications 240. In addition, these web applications 240 can be controlled by a homeowner 242, an alarm security system or company 248, or a security guard 242.

Figure 6B:
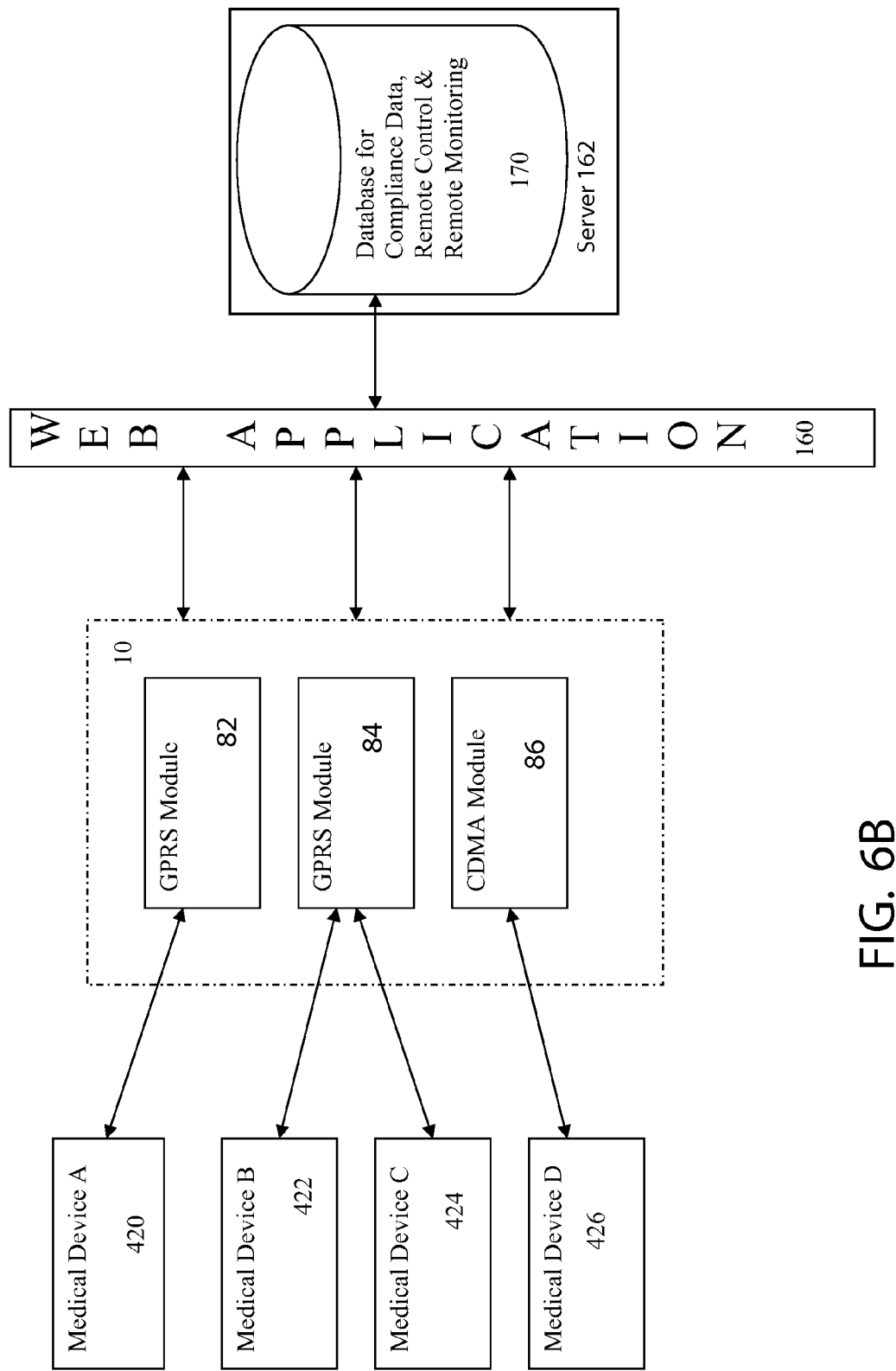
FIG. 6B discloses a scalable system showing multiple GPRS modules that communicate with web applications and with a database and also with multiple medical devices.

In this case, FIG. 6B discloses multiple GPRS modules 82, 84, and a CDMA module 86 that communicates through internet 160 or web applications, wherein these web applications are also in communication with the database 170. Each of these modules can be in communication with any one of a plurality of different medical devices. For example there can be a total of four different medical devices such as medical device A 420, medical device B 422, medical device C 424, and medical device D 426. With this design, a single database and a single device can control multiple communication modules such as GPRS modules or CDMA modules wherein each GPRS or CDMA module can then be used control multiple medical devices. In this way, this system creates a scalable system such that a single database can control multiple GPRS modules and multiple medical devices simultaneously. If the GPRS modules are similar to that which was shown in FIG. 1, then this type of GPRS module is addressable and has a particular communication identity by virtue of its SIM card. An individual user can select which GPRS module to communicate with and then call that particular GPRS module via any one of the SIM cards 46 or 48. Each GPRS module would then have its own phone number or address for individual communication.

Figure 7:
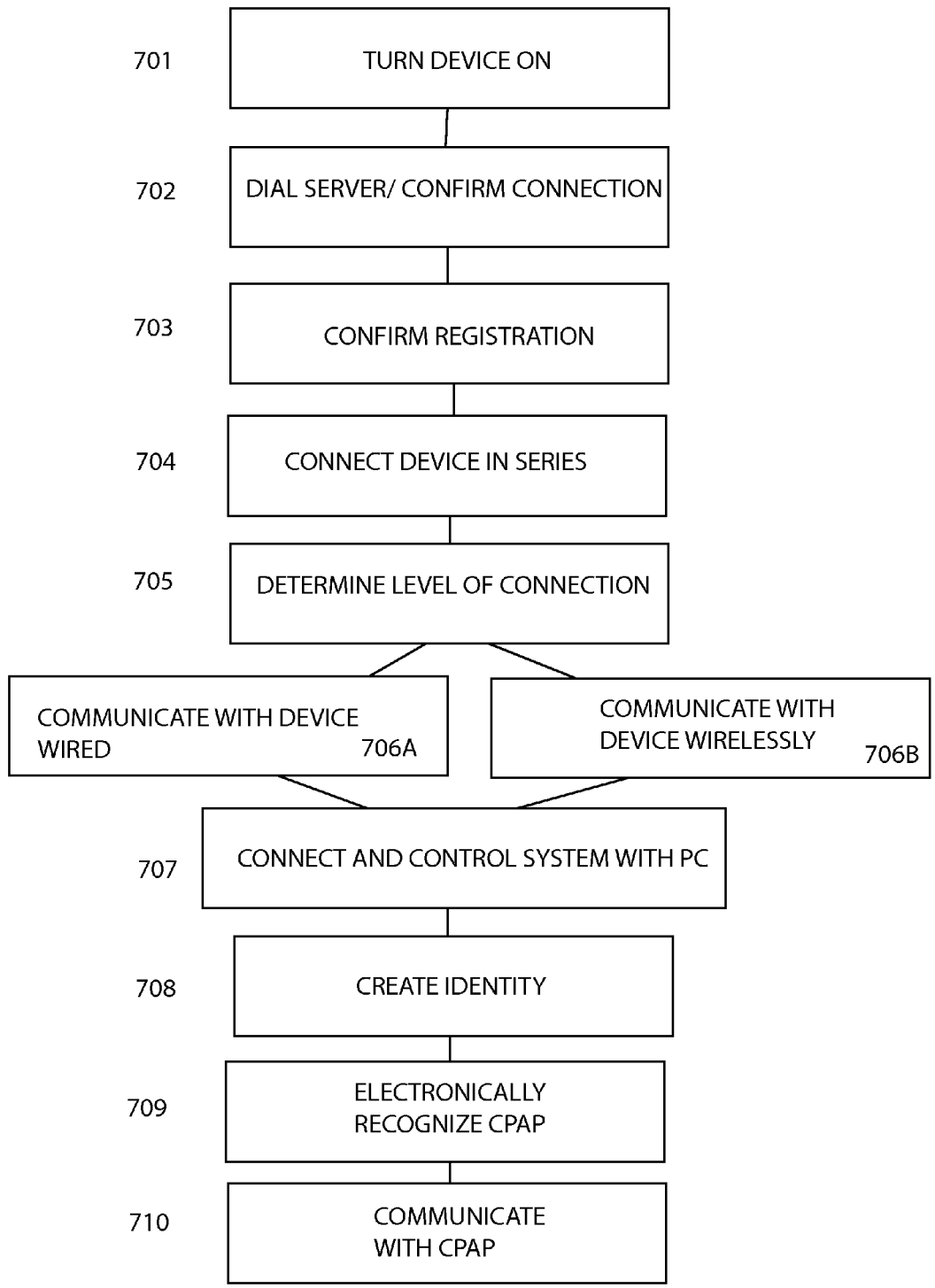
FIG. 7 is a flow chart for the process for monitoring and registering the device shown in FIG. 1A.

FIG. 7 shows a flow chart for the process for registering and controlling device 10. Device 10 can operate as follows, for example, the user can turn device 10 on, in step 701 wherein the device 10 automatically dials the GPRS or CDMA modules 82, 84, or 86, in step 702 to communicate with a modem on remote server 162 to create a handshake protocol with a remote server 162 via Internet 160. Next, LCD screen 69 can then be used to display to the user that the registration has taken place in step 703. Next, the user can physically connect device 10 in series between a standard CPAP machine 190 and an interface or mask 191 (See FIG. 5) in step 704. Once this proper connection has been achieved LCD screen 69 can be used to read out or display, regarding the level of connection in step 705. For example, LCD screen 69 can be used to display the amount of pressure flowing through the system at that time when CPAP 190 is turned on. If a proper reading on LCD screen 69 occurs, then this results in a determination that there is no leakage. For example, if a standard CPAP machine turned on high delivers 20 cm of pressure, and the pressure reading in device 10 is approximately 20 cm, then there is no substantial leakage or loss in the physical connection of the hoses.

Step 706 is an optional step and includes step 706a or step 706b. For example, step 706a involves connecting, a cable between the two devices such that a RS232 cable, a USB cable, a serial cable or any other type of cable can be used to connect the two devices 10 and 190. Once the cables are connected together, device 10 through microprocessor 23 and the communication lines can then control CPAP machine 190 to regulate the level of output. In step 706b, another type of connection can also occur in that this device 10 can also remotely control another CPAP machine either wirelessly or in a wired condition regardless of whether device 10 is fluidly connected, or connected through hoses to this CPAP machine. In that case, any one of the wireless modules such as IRDA transceiver module 24, RF transceiver module 25, a Bluetooth transceiver module 26, or any other wireless device can be used to communicate with either an onboard wireless device incorporated into an existing CPAP machine, or an add-on wireless device such as a Bluetooth dongle which can be connected to any connection port in CPAP 190 such as either a RS-232 port or a USB port.

At this point, in step 707, a user can connect to the system or device 10 through a keyboard or other type computing device such as a personal computer 200. This personal computer can be used to register or create the identity of a single device in step 708. For example, a user can connect a laptop computer 200 to device 10 either wirelessly, through any one of the wireless modules, or through any known wired modules such as a USB module 27, or RS-232 module 28. Alternatively, the user can connect generally through the internet, to server 162, which can then access device 10. Upon recognizing this connection, the user can control device 10 via computer 200 to establish a recognized identity for CPAP 190 in database 170. For example, upon creating this connection between device 10, CPAP 190 and computer 200, a user can be prompted, or could find a web page to enter in identity information regarding both the device and the CPAP machine. The identification information could relate to identification markers associated with the wireless protocols of both CPAP 190 or device 10. Alternatively, computer 200 could first recognize the identity of device 10 by its association with any one of SIM cards 46, 48, or GPRS modules 82, 84, or CDMA module 86. If device 10 is in wired connection with CPAP 190, device 10 could recognize that particular CPAP 190 via its connection to a particular wired connection port such as a particular RS-232 port.

If more than one CPAP machine is coupled to device 10 at the same time, such as CPAP 190 and an additional CPAP 191, then this device 10 which can have optional control buttons 72 and 74 for scrolling up or down among different selections on LCD display 69.

Regardless of whether the device is fluidly connected, device 10 next performs an optional series of steps in step 709 to electronically recognize CPAP 190. Device 10 can have a standard set of drivers for the most common CPAP machines pre-installed in its memory. These drivers can be used to recognize the connected CPAP machine. If the CPAP machine is an uncommon or new model, then additional drivers can be created and then uploaded from server 162 to device 10 so that device 10 can now recognize CPAP 190.

If device 10 is not fluidly connected to a CPAP machine, this device can still turn an ordinary CPAP machine into either a BiPAP or an auto adjusting CPAP machine by controlling a blower 195 on this CPAP machine by taking control of processor 192 on CPAP 190. Thus, in step 710 communication, either wireless or wired from device 10, can be transmitted via one of the wired connections 194, or wireless connections 196 to send instructions to processor 192. In this CPAP machine 190, processor 193 can then be used to control blower 195 to alternately raise or lower, the level of this blower 195.

Alternatively, CPAP 190 could be in the form of a "dumb" CPAP which cannot be electronically controlled. In this case, as long as device 10 is fluidly connected to CPAP 190, then device 10 could be used to modify the air or fluid output of CPAP 190 without controlling CPAP processor 192.

Figure 8:
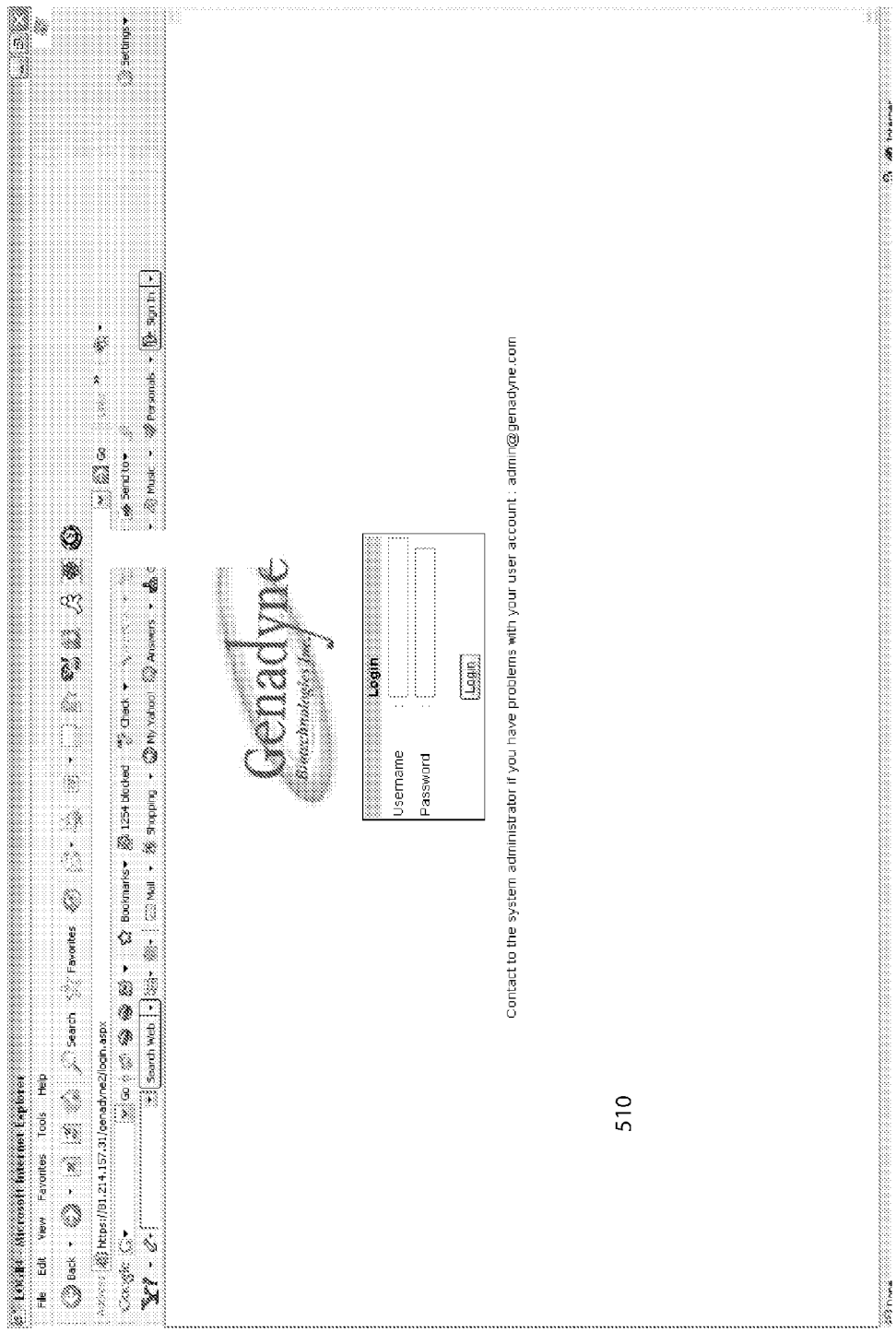
FIG. 8 discloses a login page for logging into a control system for controlling the GPRS module.

The remote control device 10 can be operated via a server. The server can then create web pages which allows a single user from a remote location to control any type of device such as a medical device. For example, FIG. 8 discloses a login page for logging into a control system for controlling the GPRS module.

Figure 9:
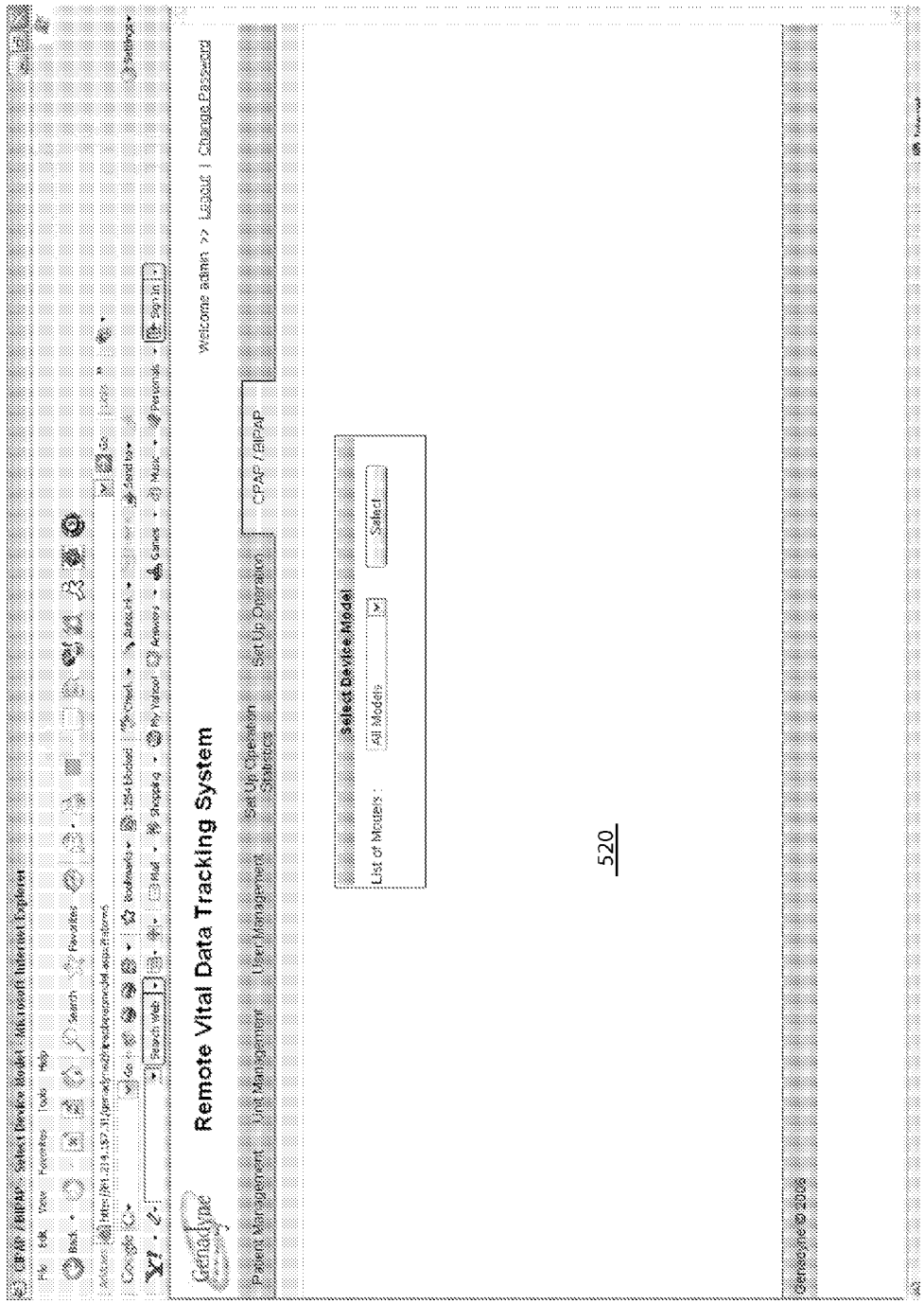
FIG. 9 shows a selection page for allowing a user to selecting among different models of a CPAP or BiPAP machine.

In addition, there is shown in FIG. 9, a selection page 520, wherein in this case a user is capable of selecting among different models of a CPAP or BiPAP machine. With this design, a remote control user can then select among different machines to control. For example a single user on a single database 170 can, through Web applications or the interne 160, control multiple different GPRS or CDMA modules 82, 84, or 86 to then control multiple different medical devices such as medical device A 420, medical device B 422, medical device C 424, or medical device D 426.

Figure 10:
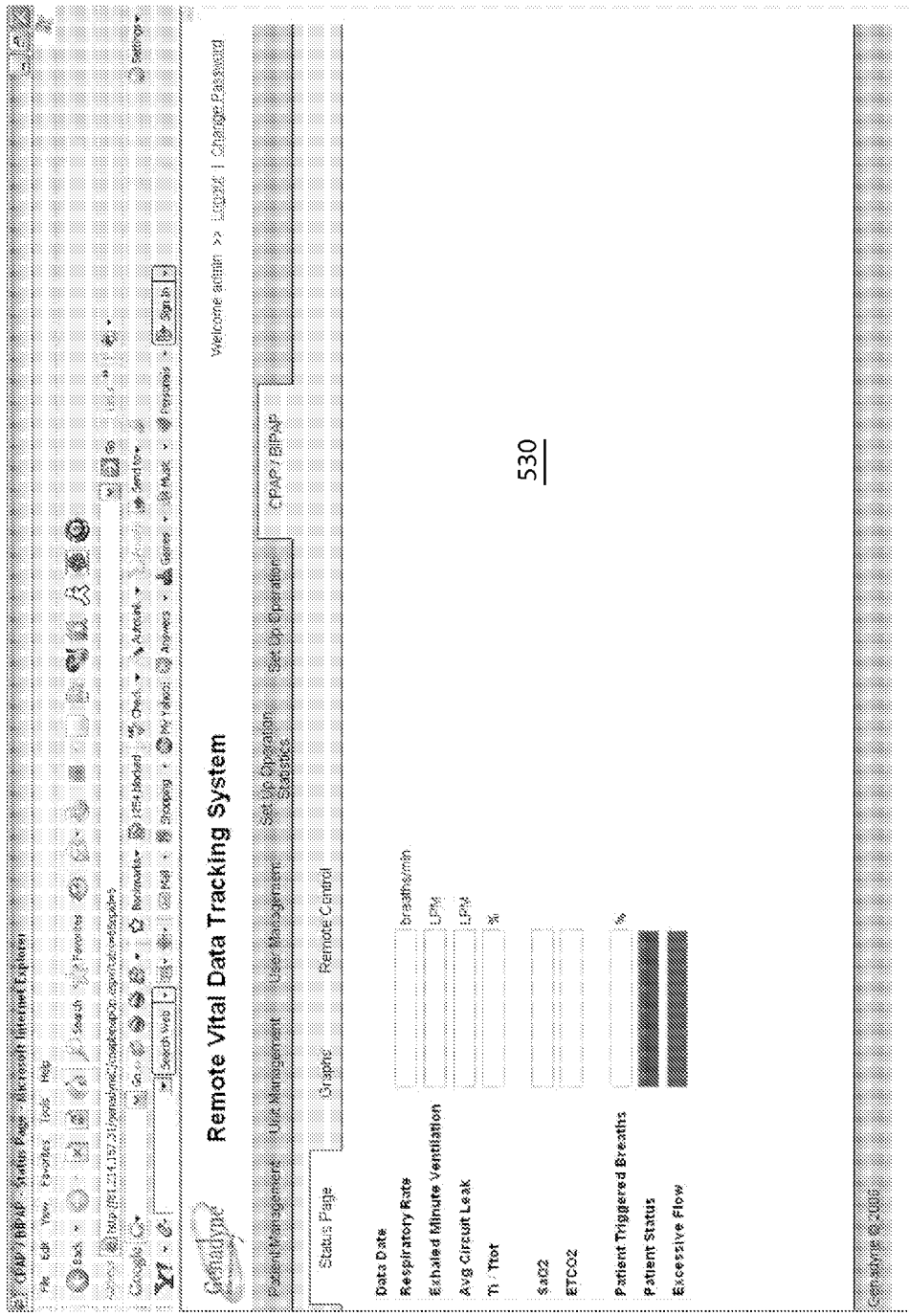
FIG. 10 discloses a status page which discloses the different characteristics of a user using a CPAP/BIPAP machine.

FIG. 10 discloses a status page 530 which is essentially a readout from a BiPAP machine at an instant moment. This readout reveals different characteristics of a user on a CPAP/BIPAP machine. In this view, information about a particular patient can be displayed on web page 530 to allow remote user to review status for particular patient. In this case, information from a particular CPAP or BiPAP machine is sent through GPRS Gateway 10 through the Internet 160 to database 170 as disclosed in FIG. 4. This record of information is then displayed on a web page 530.

Figure 11:
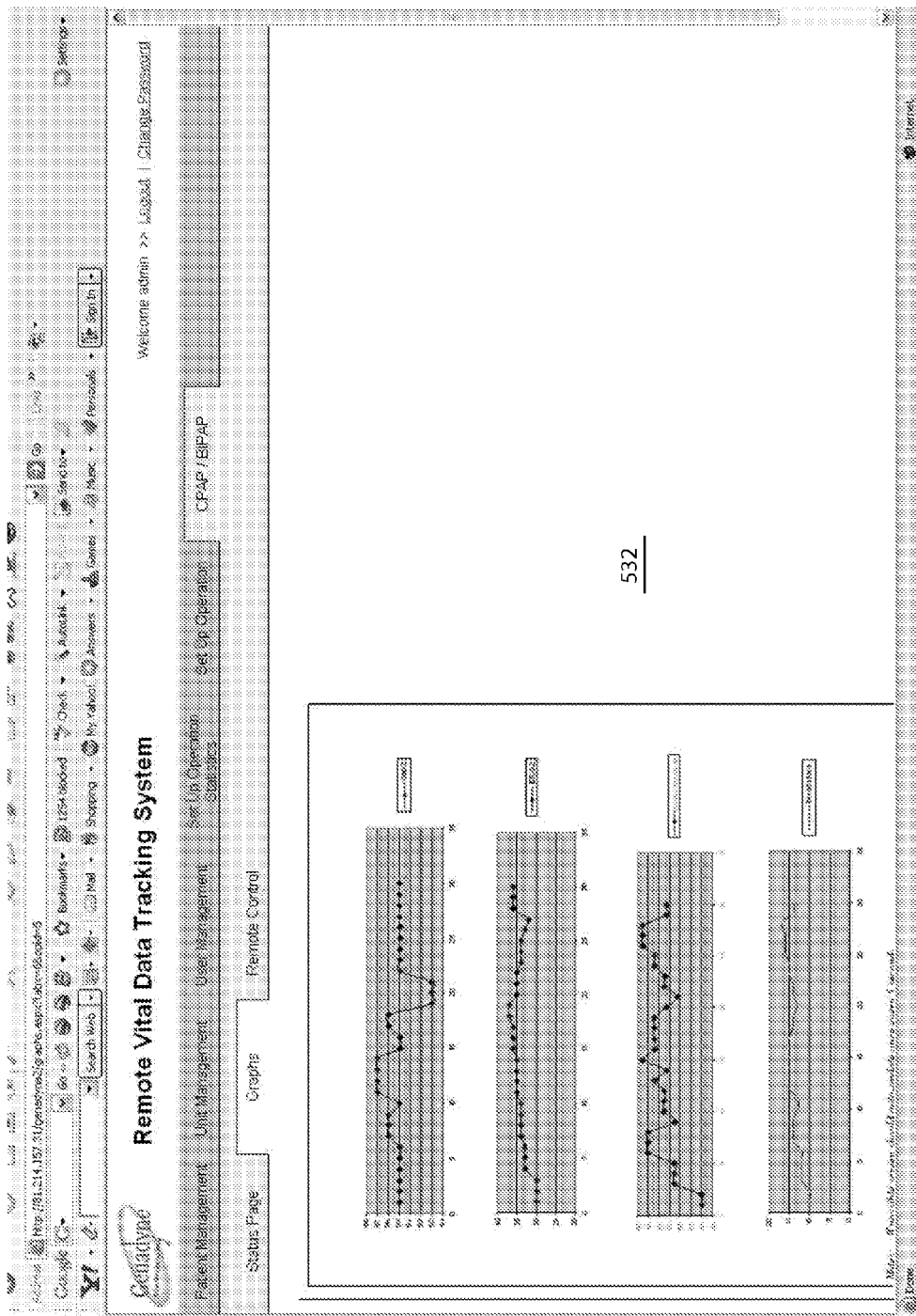
FIG. 11 discloses a web page which discloses a remote vital data tracking system.

FIG. 11 discloses a web page 532 which discloses a dynamic readout of the information displayed on web page 530. In this view, there is a remote vital data tracking system which can include a plurality of different graphs for registering readings of a user. These graphs can show different readings such as the breath rate, oxygen intake or other diagnostic features.

Figure 12:
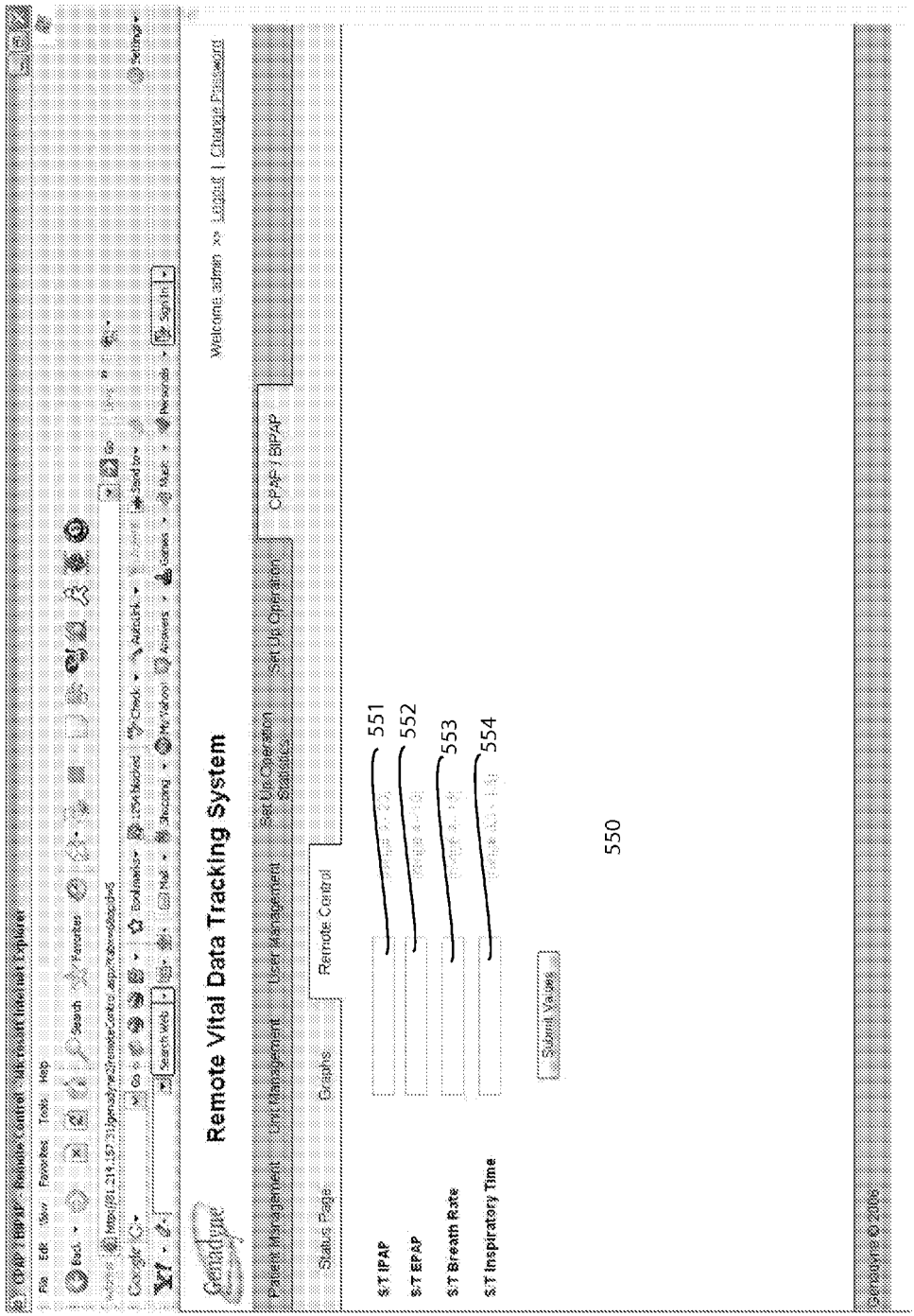
FIG. 12 discloses a remote vital data Tracking System for controlling a device.

FIG. 12 discloses a web page 550 for allowing a user to remotely control a medical device such as a CPAP machine. With this page, additional information such as the range for the standard timed inspiratory positive airway pressure (S/T IPAP), the range for the standard timed expiratory positive airway pressure, or (S/T EPAP), the range for the S/T or standard timed breath rate, such as breaths per minute, and the range for the S/T or standard timed inspiratory Time can be inserted and used to control a remote CPAP machine. The input into the fields such as fields 551, 552, 553, and 554, can be used to set the monitoring parameters for a user.

Figure 13:
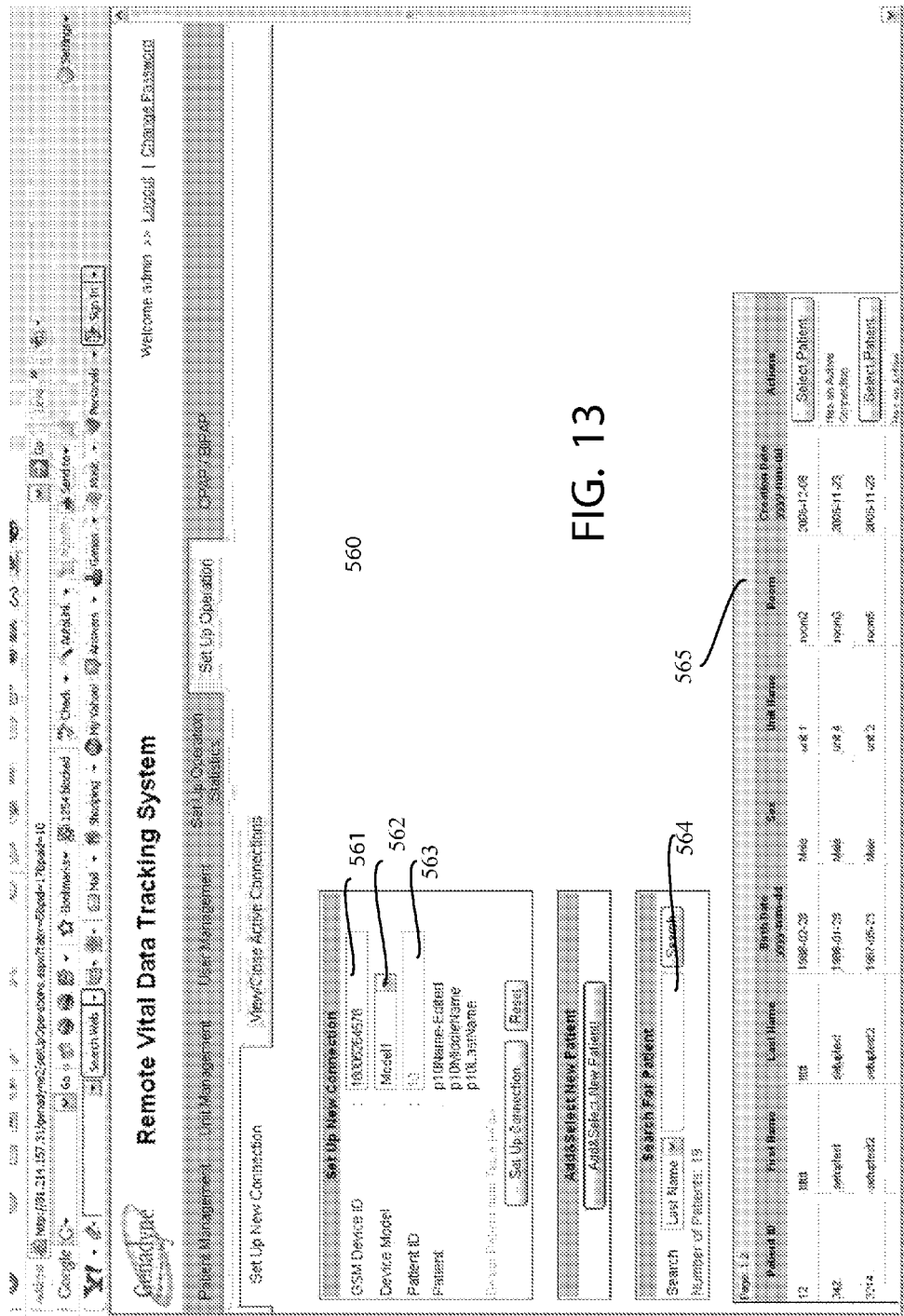
FIG. 13 discloses a remote vital data tracking system for assigning a patient to a device.

FIG. 13 discloses a remote vital data tracking system which discloses vital information about one or more patients via a particular GSM device. Each GSM or GPRS module or CDMA module has an associated identity which can be selected by this web page so that each individual GPRS or CDMA device can be individually controlled from a remote location via device ID prompt 561. The other selection features can include selection prompts for a device model 562, for a patient ID 563, which can be used to select a particular patient. There can also be an input field for allowing a user to search for a particular patient as well. Each patient can be displayed in a display section 565.

Once all of the settings have been established, the monitoring and control of this CPAP machine can be achieved through a series of additional steps. For example, the location of device 10 is updated periodically to server 162 and stored in database 170. This location is obtained via GPS tracking module 32 which is used to establish the location of device 10. During this time, medical information which is obtained from an associated patient, such as through any one of the devices 110-146 shown in FIG. 3 can be transferred either through a wired condition or wirelessly to device 10. This information is then extracted, and sent either as a single stream of date or as multiple separate streams of data through any one of SIM cards 46, or 48 or the associated GPRS modules 82, 84, or through CDMA module 86. Different sets of information such as blood pressure, temperature, oxygen levels, can either be kept separate or divided in processor 23, such that device 10 keeps an updated steady stream of data flowing to server 162. For example, the different sets of data could be sent via a single communication protocol such as through a single GPRS gateway or a single CDMA gateway, in a staggered manner. Therefore, while a continuous stream of data, could be transmitted, the communication could be in the form of a set of blood pressure data, a set of oxygen data, a set of temperature data, a set of pulse data, a set of EKG data, that is periodically updated wherein this stream of data is sent such that each vital sign is updated separately at five second intervals. Alternatively, if a user operating server 162 wanted faster updates, additional GPRS modules such as GPRS module 84, or CDMA module 86 could be used to improve the responsiveness of the system. Alternatively, all diagnostic information being sent from device 10 to server 162 could be sent out from one module while all incoming commands from server 162 could be sent through another module.

Figure 14:
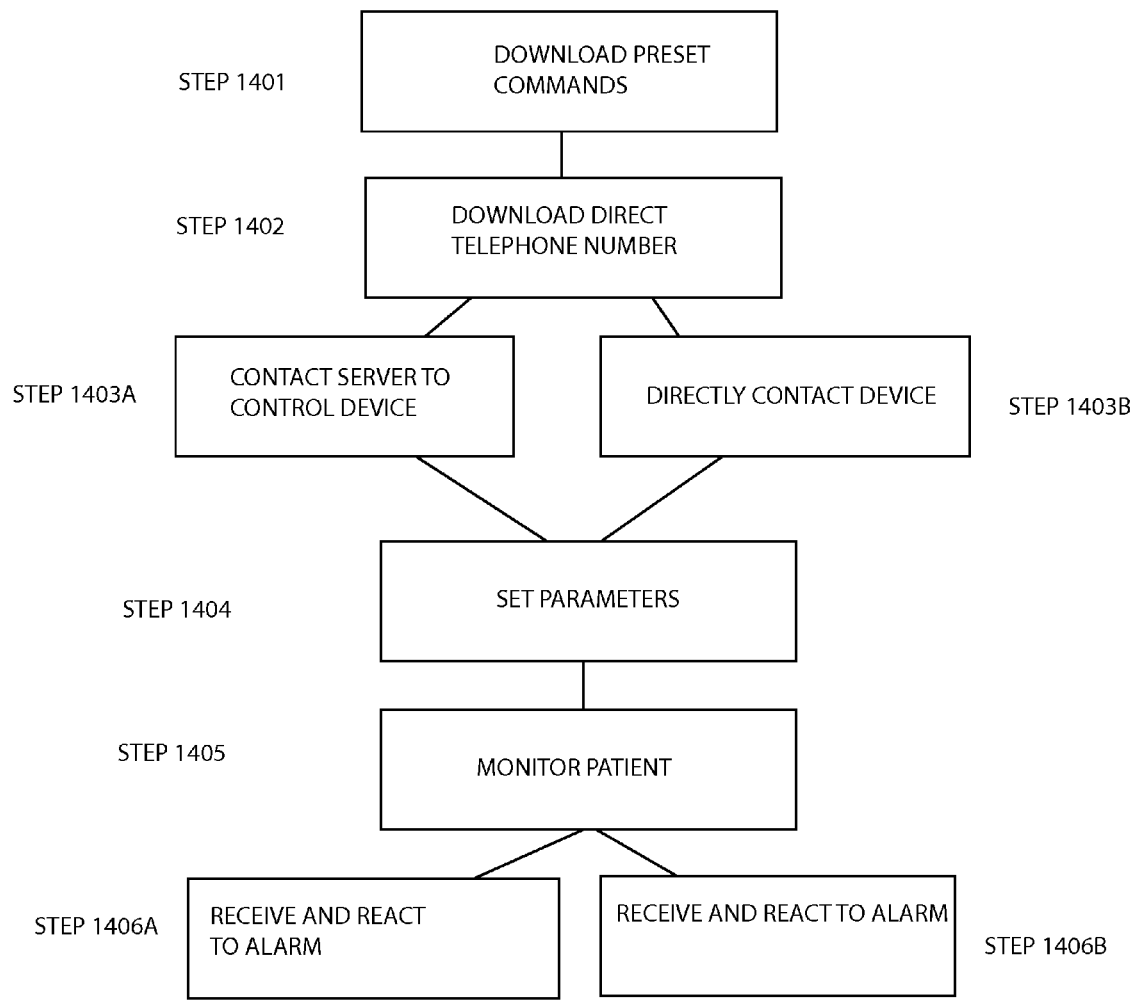
FIG. 14 discloses a flow chart for adjusting and monitoring a patient over a telecommunication protocol.

During this time, doctors can monitor their patients. For example, because this system or device 10 can operate on a cellular network, device 10 can communicate directly with a cell phone or a doctor's pager direction. Alternatively, the device 10 can communicate over the network with the server 162, wherein server 162 can then directly call a doctor's cell phone number. In this case, a single GPRS module such as GPRS module 82 or 84 can send text information as well as make phone calls simultaneously on a single module at one time. With this system, as disclosed in FIG. 12, a user can control device 10 through a web page, or that user can control device 10 via a cell phone instead. In this case, as shown in FIG. 14, there can be a series of steps for remotely controlling device 10 via a cell phone or a computer. For example, in step 1401, a user can download a set of predetermined commands to his or her cell phone. These predetermined commands can then be formed as a menu of commands allowing a user to easily select different options for device 10. For example, this user such as a doctor can input a command to increase or decrease or reset a range of the ST/IPAP rate such as disclosed in field 551, to increase or decrease or reset a range of the ST EPAP rate such as disclosed in field 552; to increase or decrease or reset a range of the breath rate 553, to increase or decrease or reset a range of a S/T inspiratory time such as disclosed in field 554.

These commands can be in the form of short-cuts on a cell phone for sending these commands. Next, in step 1402, either simultaneously, before or after this setup a user can download from server 162 a telephone number of a particular GPRS module or CDMA module on device 10 so that a user can then directly dial device 10 and then control device 10. Next, in step 1403A, a user can either contact server 162 to control device 10 or directly dial device 10 in step 1403B to form a communication connection with device 10. Alternatively, the user can contact server 162 via any known means including a personal computer connected to internet 160. In step 1404, the user can then control this device with the commands downloaded in step 1401. During this step (step 1404) the user can set the proper parameters for his or her patient. Next, in step 1405, the patient is monitored. This step of monitoring can include sending information to server 162, to remote telephone 172, (See FIG. 5) or send this information to both devices via each of the GPRS modules or CDMA modules. If a patient is being monitored on device 10, via any one of the medical devices 110-146, has vital signs that fall outside a preset monitoring range, which is stored in database 170 or in the memory of either SIM card 42 or 44 or in flash memory 59, device 10 (step 1406a) or server 162 (step 1406b) can directly contact a remote doctor on cellular telephone 172 to warn that doctor. If the device 10 has an additional CDMA or GPRS module, that module can call 911 or any other emergency system to warn the proper authorities that a patient is in distress. The information that is sent with this alarm can be the location of device 10 via the reading of GPS tracking module 32, as well as the vital signs that fall outside of this pre-set range.

Thus, with this design, a user can control one or more GPRS modules, wherein each of these GPRS modules can then be used to control a medical device. In the case of a CPAP or BiPAP machine, this type of GPRS module can then be used to turn an ordinary CPAP machine into a remote controlled auto-adjusting CPAP machine. The optional double-sided motherboard design with at least one SIM card then creates a compact and portable component that can be placed in compact spaces next to a CPAP machine or any other useful medical device and used to communicate remotely with off-site controllers via a GPRS gateway or the interne.

Accordingly, while a few embodiments of the present invention have been shown and described, it is to be understood that many changes and modifications may be made thereunto without departing from the spirit and scope of the invention as defined in the appended claims.

What is claimed is:

1. A system for controlling a PAP (Positive Airway Pressure) machine comprising:
   a) a PAP machine;
   b) at least one output tube coupled to said PAP machine;
   c) a device for controlling a fluid output of said PAP machine comprising:
      i) at least one fluid input coupled in series with said PAP machine via said output tube of said PAP machine;
      ii) at least one fluid output;
      iii) at least one flow meter disposed in a housing and coupled to said fluid input and to said fluid output;
      iv) at least one electro-mechanical valve, disposed in said housing and coupled to said fluid input and to said fluid output;
      v) at least one cellular communication module for providing remote cellular communication for said device wherein said at least one cellular communication module has a memory for storing a program for controlling at least one processor, and wherein said at least one flow meter reads a flow rate of fluid flowing through the device wherein said reading is forwarded to said at least one processor, and wherein said at least one processor compares said reading to a set of stored values in said memory;
      vi) at least one processor for controlling said at least one flow meter, said at least one electromechanical valve, and said at least one cellular communication module, wherein said at least one processor receives instructions from a remote control device via said cellular communication module wherein said instructions are for adjusting said electro-mechanical valve, to control an amount of fluid dispersed by said at least one fluid output;
      vii) at least one additional cellular communication module, wherein said at least one additional cellular communication module is in communication with said at least one processor;
      viii) a motherboard comprising a first side and a second side, wherein said first side has said processor, said at least one cellular communication module, and said at least one additional cellular communication module disposed thereon, and wherein said second side has said at least one flow meter, and said at least one electro-mechanical valve disposed thereon; and
   d) at least one switch for converting from non-autoadjust to autoadjust settings.

2. The system as in claim 1, wherein said fluid is air, and wherein the system further comprises a database stored separate from said housing, on a server.

3. The system as in claim 2, further comprising at least one motherboard wherein said system comprises a housing, and further comprises the following components:
   a motherboard, wherein said processor is a microprocessor that is coupled to said motherboard, wherein the system further comprises:
      at least one USB communication module coupled to said motherboard; at least one flashcard communication module coupled to said motherboard;
      at least one RF transceiver module;
      at least one cellular communication module comprising at least one SIM card configured to connect to said at least one cellular communication module;
      at least one GPS tracking module;
         wherein said microprocessor is programmed to perform the following steps:
            connect with said at least one database;
            download preset commands;
            set a plurality of parameters for a patient; and
            monitor a patient.

4. The system as in claim 3, wherein said processor is configured to automatically adjust a setting for fluid flow when reading a change in a predetermined setting from said database.

5. The system as in claim 3, wherein said cellular communication module is configured to communicate on at least one of a CDMA or GSM network.

6. The system as in claim 5, wherein said microprocessor is programmed to perform the following additional step:
   switch communication to a cellular communication module that has a highest signal strength.

7. The system as in claim 3, wherein said microprocessor is programmed to provide an alarm if a patient's actual parameters are outside of any of said plurality of parameters for a patient.

8. The system as in claim 3, wherein said microprocessor is programmed to perform the following additional step:
   determine a signal strength of said at least two cellular communication modules.

9. The system as in claim 3, wherein said processor is programmed to perform the following additional step:
   allocating data sets to at least two different communication protocols.

10. The system as in claim 3, wherein said microprocessor is configured to control said electromechanical valve to control an output pressure of fluid flowing from said housing.

11. The system as in claim 10, wherein said microprocessor is configured to control said electromechanical valve so as to control both an input air pressure and an output air pressure in communication with a patient, wherein said processor is configured to switch from controlling a single level of air flow to controlling multiple levels of air flow.

12. The system as in claim 1, wherein said device further comprises a housing, wherein said motherboard is disposed in said housing, and wherein said housing has at least one slot for inserting and removing at least one cellular communication module.

13. The system as in claim 1, wherein said device further comprises an LCD display which is in communication with said motherboard and said at least one processor.

14. The system as in claim 1, wherein said device further comprises at least one wired communication module.

15. The system as in claim 14, wherein said PAP machine further comprises at least one wired communication module, wherein at least one wired communication module on said device is in communication with said at least one wired communication module on said pap machine to control said PAP machine.

16. The system as in claim 1, wherein said device further comprises at least one additional wireless communication module.

17. The system as in claim 16, wherein said PAP machine further comprises at least one wireless communication module, wherein said at least one wireless communication module on said device is in communication with said at least one wireless communication module on said PAP machine to control said pap machine.

18. The system as in claim 1, wherein said at least one processor is configured to adjust said valve in the device to change an output pressure sent from the device.

* * * * *